US012116133B2

(12) United States Patent
Larsen et al.

(10) Patent No.: US 12,116,133 B2
(45) Date of Patent: Oct. 15, 2024

(54) VENTILATION ASSEMBLY IN AN AIRCRAFT

(71) Applicant: The Boeing Company, Chicago, IL (US)

(72) Inventors: Ty Aaby Larsen, Everett, WA (US); Eric Anthony Hill, Everett, WA (US); Daniel T. Sim, Everett, WA (US); James Jason Salmon, Kirkland, WA (US); James P. Schalla, Mercer Island, WA (US); Nicholas A. Jones, Everett, WA (US); David R. Space, Everett, WA (US); Gabriel Lynn Miller, Everett, WA (US)

(73) Assignee: The Boeing Company, Chicago, IL (US)

( * ) Notice: Subject to any disclaimer, the term of this patent is extended or adjusted under 35 U.S.C. 154(b) by 418 days.

(21) Appl. No.: 17/658,607

(22) Filed: Apr. 8, 2022

(65) Prior Publication Data

US 2023/0002060 A1 Jan. 5, 2023

Related U.S. Application Data

(60) Provisional application No. 63/202,938, filed on Jun. 30, 2021.

(51) Int. Cl.
*B64D 11/06* (2006.01)
*A61L 9/00* (2006.01)
(Continued)

(52) U.S. Cl.
CPC .......... *B64D 11/0626* (2014.12); *B64D 13/06* (2013.01); *B64D 2013/0625* (2013.01); *B64D 2013/0651* (2013.01)

(58) Field of Classification Search
CPC ................ B64D 11/0626; B64D 13/06; B64D 2013/0625; B64D 2013/0651; B64D 2013/0655
See application file for complete search history.

(56) References Cited

U.S. PATENT DOCUMENTS

| 374,424 A | 12/1887 | Ober |
| 1,674,535 A | 1/1928 | Verville |

(Continued)

FOREIGN PATENT DOCUMENTS

| DE | 3333878 A1 | 3/1985 |
| DE | 102020131653 A1 * | 6/2022 |

(Continued)

OTHER PUBLICATIONS

Werthmann, DE102020131653 and translation (Year: 2022).*

(Continued)

*Primary Examiner* — Steven S Anderson, II
(74) *Attorney, Agent, or Firm* — Yee & Associates, P.C.

(57) ABSTRACT

A ventilation assembly comprises a number of fan systems configured to purify air and a number of air distribution assemblies. Each air distribution assembly of the number of air distribution assemblies is configured to be removably installed on a seatback of a passenger seat. Each air distribution assembly of the number of air distribution assemblies comprises a pair of air distribution vents, ductwork configured to receive air from at least one fan system of the number of fan systems and direct air to the pair of air distribution vents, and a seat attachment device configured to removably couple the pair of air distribution vents to the seatback such that each air distribution vent is situated on opposite sides of the seatback for providing purified air to a seated passenger.

45 Claims, 24 Drawing Sheets

(51) Int. Cl.
 *B60N 2/90* (2018.01)
 *B64D 13/06* (2006.01)

(56) References Cited

U.S. PATENT DOCUMENTS

| | | | |
|---|---|---|---|
| 3,097,505 | A | 7/1963 | Smith |
| 3,112,002 | A | 11/1963 | van der Lely |
| 3,375,638 | A | 4/1968 | Dungler et al. |
| 3,537,447 | A | 11/1970 | Gauthier et al. |
| 3,724,172 | A | 4/1973 | Wood |
| 4,023,472 | A | 5/1977 | Grunder et al. |
| 4,035,018 | A | 7/1977 | Erbele et al. |
| 4,114,521 | A | 9/1978 | Busch |
| 4,376,408 | A | 3/1983 | Iijima et al. |
| 4,412,849 | A | 11/1983 | Shahani |
| 4,440,164 | A | 4/1984 | Werjefelt |
| 4,461,155 | A | 7/1984 | Werjefelt |
| 4,559,939 | A | 12/1985 | Levine et al. |
| 4,581,988 | A | 4/1986 | Mattei |
| 4,612,975 | A | 9/1986 | Ikari |
| 4,742,760 | A | 5/1988 | Horstman et al. |
| 4,751,919 | A | 6/1988 | Thomsen |
| 4,766,893 | A | 8/1988 | Drews |
| 4,819,548 | A | 4/1989 | Horstman |
| 4,832,287 | A | 5/1989 | Werjefelt |
| 4,881,456 | A | 11/1989 | Yasuda et al. |
| 5,007,421 | A | 4/1991 | Stewart |
| 5,102,189 | A | 4/1992 | Saito et al. |
| 5,160,517 | A | 11/1992 | Hicks et al. |
| 5,299,763 | A | 4/1994 | Bescoby et al. |
| 5,450,894 | A | 9/1995 | Inoue et al. |
| 5,832,919 | A | 11/1998 | Kano et al. |
| 5,997,091 | A | 12/1999 | Rech et al. |
| 6,012,297 | A | 1/2000 | Ichishi et al. |
| 6,019,676 | A | 2/2000 | Kim |
| 6,080,059 | A | 6/2000 | Kim |
| 6,179,706 | B1 | 1/2001 | Yoshinori et al. |
| 6,189,966 | B1 | 2/2001 | Faust et al. |
| 6,196,627 | B1 | 3/2001 | Faust et al. |
| 6,241,598 | B1 | 6/2001 | Kleissler, Jr. |
| 6,277,023 | B1 | 8/2001 | Schwarz |
| 6,293,860 | B1 | 9/2001 | Kim |
| 6,340,024 | B1 | 1/2002 | Brookman et al. |
| 6,372,101 | B1 | 4/2002 | Barrese et al. |
| 6,491,254 | B1 | 12/2002 | Walkinshaw et al. |
| 6,604,785 | B2 | 8/2003 | Bargheer et al. |
| 6,626,971 | B1 | 9/2003 | Forbert et al. |
| 6,644,735 | B2 | 11/2003 | Bargheer et al. |
| 6,659,689 | B1 | 12/2003 | Courtney et al. |
| 6,685,553 | B2 | 2/2004 | Aoki |
| 6,744,898 | B1 | 6/2004 | Hirano |
| 6,746,076 | B2 | 6/2004 | Bogisch et al. |
| 6,761,399 | B2 | 7/2004 | Bargheer et al. |
| 6,910,961 | B2 | 6/2005 | Niu |
| 6,928,829 | B2 | 8/2005 | Kamiya et al. |
| 6,976,734 | B2 | 12/2005 | Stoewe |
| 7,037,188 | B2 | 5/2006 | Schmid et al. |
| 7,080,443 | B2 | 7/2006 | Dubuc |
| 7,195,316 | B2 | 3/2007 | Shimasaki et al. |
| 7,201,441 | B2 | 4/2007 | Stoewe et al. |
| 7,213,876 | B2 | 5/2007 | Stoewe |
| 7,275,984 | B2 | 10/2007 | Aoki |
| 7,300,499 | B1 | 11/2007 | Fleisher |
| 7,399,037 | B2 | 7/2008 | Schumacher et al. |
| 7,419,214 | B2 | 9/2008 | Plant |
| 7,506,924 | B2 | 3/2009 | Bargheer et al. |
| 7,531,017 | B2 | 5/2009 | Ryan et al. |
| 7,581,785 | B2 | 9/2009 | Heckmann et al. |
| 7,621,594 | B2 | 11/2009 | Hartmann et al. |
| 7,708,626 | B2 | 5/2010 | Bargheer et al. |
| 7,789,346 | B2 | 9/2010 | Horstman et al. |
| 7,871,038 | B2 | 1/2011 | Space et al. |
| 7,873,451 | B2 | 1/2011 | Hartmann et al. |
| 8,003,058 | B2 | 8/2011 | Bergeron et al. |
| 8,206,475 | B2 | 6/2012 | Walkinshaw |
| 10,029,797 | B2 | 7/2018 | Space et al. |
| 2002/0041116 | A1 | 4/2002 | Bogisch et al. |
| 2002/0076059 | A1 | 6/2002 | Joynes |
| 2004/0168459 | A1 | 9/2004 | Blackstone |
| 2004/0195446 | A1* | 10/2004 | Smallhorn ....... B64D 11/00155 |
| | | | 244/118.5 |
| 2005/0016199 | A1 | 1/2005 | Blackstone |
| 2005/0178138 | A1 | 8/2005 | Blackstone |
| 2005/0282486 | A1 | 12/2005 | Takeda et al. |
| 2006/0032265 | A1 | 2/2006 | Shaw |
| 2006/0079168 | A1 | 4/2006 | Goldsmith |
| 2006/0267383 | A1 | 11/2006 | Bargheer et al. |
| 2007/0068520 | A1 | 3/2007 | Laib et al. |
| 2007/0266855 | A1 | 11/2007 | Fleisher |
| 2008/0066484 | A1 | 3/2008 | Blackstone |
| 2008/0099606 | A1 | 5/2008 | Horstman et al. |
| 2008/0170971 | A1 | 7/2008 | Bergeron et al. |
| 2008/0175426 | A1 | 7/2008 | Jacobs |
| 2008/0191520 | A1 | 8/2008 | Harmann et al. |
| 2008/0308106 | A1 | 12/2008 | Augustine et al. |
| 2008/0315634 | A1 | 12/2008 | Hartmann et al. |
| 2009/0017742 | A1 | 1/2009 | Diaks |
| 2009/0044800 | A1 | 2/2009 | Jorn |
| 2009/0134675 | A1 | 5/2009 | Pfahler |
| 2009/0139519 | A1 | 6/2009 | Deutscher et al. |
| 2010/0043794 | A1 | 2/2010 | Saito et al. |
| 2010/0081369 | A1 | 4/2010 | Space et al. |
| 2012/0199003 | A1 | 8/2012 | Melikov et al. |
| 2013/0040546 | A1 | 2/2013 | Noske et al. |
| 2014/0179212 | A1* | 6/2014 | Space ............... B60N 2/5635 |
| | | | 454/76 |
| 2014/0363333 | A1 | 12/2014 | Carr |
| 2020/0010197 | A1* | 1/2020 | Otovic ............. B60N 2/5883 |
| 2020/0122614 | A1* | 4/2020 | Kawano ........... B60H 1/00285 |
| 2020/0198506 | A1 | 6/2020 | Longatte et al. |

FOREIGN PATENT DOCUMENTS

| | | | |
|---|---|---|---|
| EP | 0217752 A2 | 4/1987 | |
| EP | 1600375 A1 * | 11/2005 | ............... A47C 7/74 |
| FR | 2592617 A1 | 7/1987 | |
| JP | S60174314 A | 9/1985 | |
| JP | H1159597 A | 3/1999 | |

OTHER PUBLICATIONS

Bauer, EP1600375 and translation (Year: 2005).*
"Cleaning aircraft-cabin air: Breathing more easily," The Economist, Sep. 17, 2009, 3 pages. Accessed Jul. 1, 2013, http://www.economist.com/node/14446718.
Hunt et al., "The Airplane Cabin Environment—Issues Pertaining to Flight Attendant Comfort," Presented at the International In-flight Service Management Organization Conference, Montreal, Canada, Nov. 1994, 12 pages.
European Patent Office, Extended Search Report, dated Nov. 24, 2022, regarding Application No. EP22182168.9, 9 pages.

* cited by examiner

VENTILATION ASSEMBLY IN AN AIRCRAFT

RELATED PROVISIONAL APPLICATION

This application claims the benefit of priority of provisional U.S. Patent Application Ser. No. 63/202,938, entitled "Ventilation Assembly in an Aircraft", filed on Jun. 30, 2021, which is hereby incorporated by reference.

BACKGROUND INFORMATION

1. Field

The present disclosure relates generally to aircraft and in particular to a method and apparatus for managing air quality in an aircraft. Still more particularly, the present disclosure relates to a method and apparatus for providing personal ventilation in an aircraft.

2. Background

Cabin air systems, in currently available aircraft, are designed to provide a safe and comfortable cabin environment at cruising altitudes. These cruising altitudes can reach upwards of 40,000 feet. At these altitudes, the aircraft cabin is pressurized to enable the passengers and crew to breathe normally. Air enters a passenger area from overhead distribution outlets that run the length of the passenger cabin.

These outlets can be designed to generate circular airflow patterns within the cabin. Air can be exhausted through air returns located in sidewalls near the floor of the cabin. These grills can be located along the length of the cabin and on both sides of the cabin. Air can be supplied and exhausted from the passenger area on a continuous basis. Current personal air distribution nozzles include gaspers located above passenger seats. However, gaspers may provide an uncomfortably high velocity of air flow that can create a draft.

Therefore, it would be desirable to have a method and apparatus that ta es into account at least some of the issues discussed above, as well as other possible issues. For example, it may be desirable to provide an alternative personal air distribution system.

SUMMARY

An embodiment of the present disclosure provides a ventilation assembly. The ventilation assembly comprises a number of fan systems configured to purify air and a number of air distribution assemblies. Each air distribution assembly of the number of air distribution assemblies is configured to be removably installed on a seatback of a passenger seat. Each air distribution assembly of the number of air distribution assemblies comprises a pair of air distribution vents, ductwork configured to receive air from at least one fan system of the number of fan systems and direct air to the pair of air distribution vents, and a seat attachment device configured to removably couple the pair of air distribution vents to the seatback such that each air distribution vent is situated on opposite sides of the seatback for providing purified air to a seated passenger.

Another embodiment of the present disclosure provides a ventilation assembly. The ventilation assembly comprises a number of fan systems configured to draw in and purify air, a manifold configured to distribute air from the number of fan systems to a number of air distribution assemblies, a number of mounting plates, and the number of air distribution assemblies. Each mounting plate of the number of mounting plates is configured to attach to a seat track of an aircraft. Each mounting plate of the number of mounting plates comprises a base configured to connect to a fan system of a number of fan systems, and a positioning feature configured to restrain the manifold. Each air distribution assembly of the number of air distribution assemblies is configured to be removably installed on a seatback of a passenger seat. Each air distribution assembly of the number of air distribution assemblies comprises a pair of air distribution vents, ductwork configured to direct air from the manifold to the air distribution vents, and a seat attachment device configured to removably couple the pair of air distribution vents to the seatback such that each air distribution vent is situated on opposite sides of the seatback for providing purified air to a seated passenger.

A further embodiment of the present disclosure provides a ventilation assembly. The ventilation assembly comprises a number of fan systems configured to draw in and purify air, a manifold configured to distribute air from the number of fan systems to a number of air distribution assemblies, a number of mounting plates, each mounting plate of the number of mounting plates configured to attach at least one of the manifold or a fan system of the number of fan systems to a seat track of an aircraft, and the number of air distribution assemblies, each air distribution assembly of the number of air distribution assemblies configured to be removably installed on a seatback of a passenger seat.

A yet further embodiment of the present disclosure provides an aircraft. The aircraft comprises a plurality of sets of passenger seats and a plurality of ventilation assemblies. Each ventilation assembly of the plurality of ventilation assemblies is associated with a respective set of passenger seats in the plurality of sets of passenger seats. Each ventilation assembly of the plurality of ventilation assemblies comprises a number of mounting plates, a number of fan systems, and a number of air distribution assemblies. Each mounting plate of the number of mounting plates attached to a respective seat track. The number of fan systems is configured to purify air. Each fan system is positioned beneath the respective set of passenger seats and connected to a base of a respective mounting plate of the number of mounting plates. Each air distribution assembly of the number of air distribution assemblies is configured to be removably installed on a seatback of a passenger seat in the set of passenger seats. Each air distribution assembly of the number of air distribution assemblies comprises a pair of air distribution vents, ductwork configured to receive air from at least one fan system of the number of fan systems and direct air to the pair of air distribution vents, and a seat attachment device configured to removably couple the pair of air distribution vents to the seatback such that each air distribution vent is situated on opposite sides of the seatback for providing purified air to a seated passenger.

A yet further embodiment of the present disclosure provides a ventilation assembly. The ventilation assembly comprises a number of fan systems mounted to a number of seat tracks in an aircraft and configured to purify air from the aircraft, and a number of air distribution assemblies pneumatically connected to the number of fan systems. Each air distribution assembly of the number of air distribution assemblies is removably installed on a seatback of a passenger seat and configured to provide air to the passenger seat and create a personal breathing space.

A still further embodiment of the present disclosure provides a method of installing a ventilation assembly. A number of fan systems is secured to a number of seat tracks and beneath a set of passenger seats in an aircraft. A number of air distribution assemblies is removably connected to seatbacks of passenger seats in the set of passenger seats. Ductwork of the number of air distribution assemblies is connected to the number of fan systems.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative examples recognize and take into account one or more different considerations. The illustrative examples recognize and take into account that current aircraft environmental control systems attempt to minimize passengers from inhaling contaminants by reducing the total number of contaminants in an aircraft cabin. A purity level of the cabin air is commonly defined as a percentage of contaminant free air in a volume of sampled air.

Cabin air purity levels generally increase when the air inside the cabin is replaced by air from outside the cabin. Obtaining more outside air to inject into the cabin has the drawback of increasing aircraft fuel consumption. To reduce aircraft fuel consumption, the aircraft industry has increasingly reduced outside airflow into the cabin. To compensate for the reduced airflow into the cabin, yet maintain allowable cabin air purity levels, the aircraft industry standard has been to add large cabin air recirculation systems that incorporate large high efficiency particulate air filters. Cabin air recirculation systems often include large and powerful fans to draw cabin air through the filters and inject the air back into the cabin. Cabin air recirculation systems can include an air distribution assembly. Current cabin air distribution assemblies tend to inject high velocity non-laminar streams of air into the aircraft cabin.

The illustrative embodiments recognize and take into account that a solution should not undesirably cause concerns for emergency egress, create head strike issues, or provide break away issues when the aircraft is in use. The illustrative embodiments recognize and take into account that integrated personal air delivery could be provided in a new aircraft design, but would require multiple years of design, testing, and production. The illustrative embodiments recognize and take into account that the illustrative embodiments provide a retrofit to current passenger seating. The illustrative embodiments recognize and take into account that the illustrative embodiments can provide the benefits equivalent to integrated air delivery designs without recertification of the passenger seats or aircraft. The illustrative embodiments recognize and take into account that the illustrative embodiments can provide the benefits equivalent to integrated air delivery designs without the time for design, testing, and production.

Figure 1:
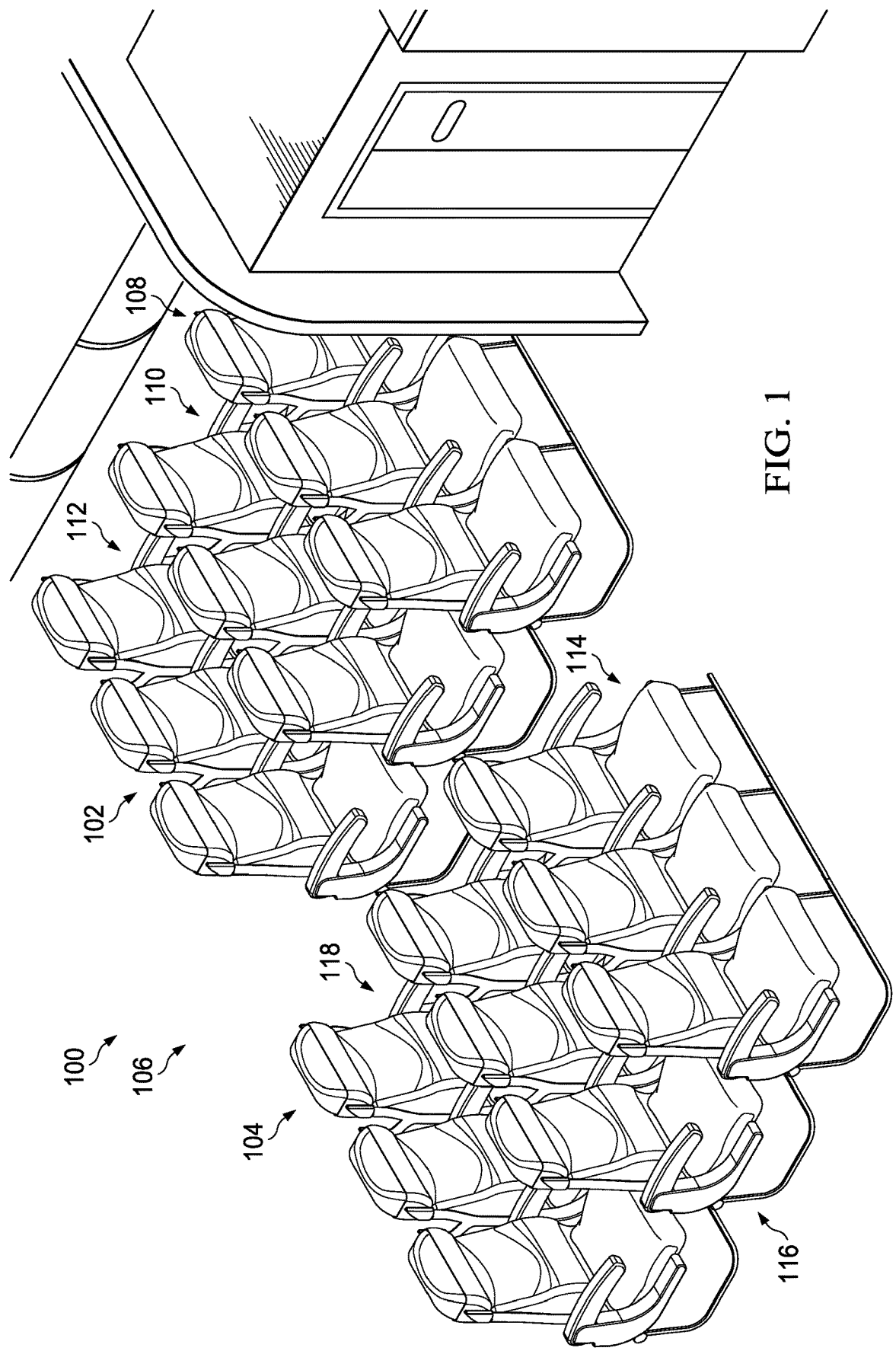
FIG. 1 is an illustration of an aircraft cabin in which an illustrative embodiment may be implemented.

Turning now to FIG. 1 is an illustration of an aircraft cabin in which an illustrative embodiment may be implemented. Aircraft 100 comprises plurality of rows of passenger seats 102 and plurality of ventilation assemblies 104 in passenger cabin 106. Each ventilation assembly of plurality of ventilation assemblies 104 is associated with a respective set of passenger seats in plurality of rows of passenger seats 102. Each set of passenger seats includes any desirable quantity of passenger seats. As depicted, each set of passenger seats comprises three passenger seats in a row of passenger seats on a single side of an aisle in passenger cabin 106. However, in other illustrative examples, a set of passenger seats includes any desirable quantity of passenger seats.

As depicted, plurality of sets of passenger seats 102 includes set of passenger seats 108, set of passenger seats 110, set of passenger seats 112, set of passenger seats 114, set of passenger seats 116, and set of passenger seats 118. As depicted, each set of passenger seats in plurality of passenger seats 102 is a row of passenger seats that has a respective ventilation assembly associated with the set of passenger seats. In some non-depicted illustrative examples, each passenger seat has its own respective ventilation assembly associated with the passenger seat.

Although, as depicted, each set of passenger seats is a row of passenger seats a set of passenger seats can include any quantity of passenger seats. In some illustrative examples, a set of passenger seats is a subset of a row of passenger seats.

A ventilation assembly of the illustrative examples can be installed in aircraft 100 without recertifying plurality of passenger seats 102. A ventilation assembly of the illustrative examples can be installed in aircraft 100 as a retrofit, after aircraft has been placed into service with an airline.

Figure 2:
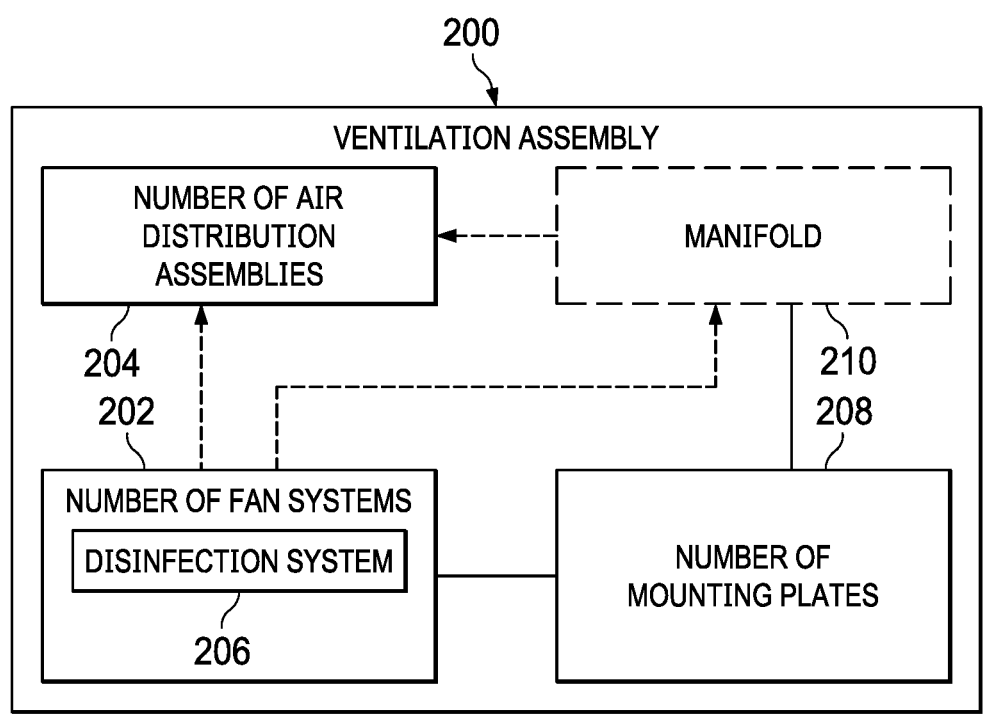
FIG. 2 is a block diagram of a ventilation assembly in accordance with an illustrative embodiment.

Turning now to FIG. 2, a block diagram of a ventilation assembly is depicted in accordance with an illustrative embodiment. Ventilation assembly 200 can be used in aircraft 100 of FIG. 1. Ventilation assembly 200 comprises number of fan systems 202 configured to purify air and number of air distribution assemblies 204. Each of number of fan systems 202 includes a respective disinfection system 206. Disinfection system 206 includes at least one of UV sanitizing equipment, an electric filter, or a mechanical air filter.

As used herein, "a number of," when used with reference to items means one or more items. For example, number of fan systems 202 includes one or more fans. In some illustrative examples, number of fan systems 202 includes only one fan system. In some illustrative examples, the quantity of fan systems in number of fan systems 202 is less than a quantity of air distribution assemblies in number of air distribution assemblies 204. In some illustrative examples, the quantity of fan systems in number of fan systems 202 is the same as the quantity of air distribution assemblies in number of air distribution assemblies 204.

As used herein, the phrase "at least one of," when used with a list of items, means different combinations of one or more of the listed items may be used and only one of each item in the list may be needed. For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations. The item may be a particular object, thing, or a category. In other words, at least one of means any combination items and number of items may be used from the list but not all of the items in the list are required.

Each air distribution assembly of number of air distribution assemblies 204 is configured to be removably installed on a seatback of a passenger seat. Each air distribution assembly of number of air distribution assemblies 204 is configured to provide purified air from number of fan systems 202 to a seated passenger.

In some illustrative examples, each air distribution assembly of number of air distribution assemblies 204 comprises a pair of air distribution vents, ductwork configured to receive air from at least one fan system of number of fan systems 202 and direct air to the pair of air distribution vents, and a seat attachment device configured to removably couple the pair of air distribution vents to the seatback such that each air distribution vent is situated on opposite sides of the seatback for providing purified air to a seated passenger. In some illustrative examples, removably connecting number of air distribution assemblies 204 to the seatbacks of the passenger seats in a set of passenger seats comprises at least one of extending or contracting an attachment system to encircle a portion of a respective seatback.

Ventilation assembly 200 is associated with a set of passenger seats. As used herein, a "set of," when used with reference to items means one or more items. For example, a set of passenger seats includes one or more passenger seats. In some illustrative examples, a set of passenger seats includes the passenger seats in a same row and on a same side of an aisle. In some illustrative examples, in first class, a set of passenger seats can be a single seat. In some illustrative examples, in business class, a set of passenger seats may include two seats. In some illustrative examples, in economy, a set of passenger seats may include up to three seats.

To reduce the weight attached to a passenger seat, number of fan systems 202 is not attached to a passenger seat. Number of fan systems 202 is connected to a number of seat tracks in the aircraft by number of mounting plates 208. Each mounting plate of number of mounting plates 208 is configured to attach to a seat track of an aircraft. Each mounting plate of number of mounting plates 208 comprises a base configured to connect to a fan system of number of fan systems 202.

In some illustrative examples, number of fan systems 202 provides air to number of air distribution assemblies 204 directly. In some other illustrative examples, manifold 210 is present. Manifold 210 is configured to distribute air from number of fan systems 202 to number of air distribution assemblies 204. In these illustrative examples, each mounting plate of number of mounting plates 208 comprises a positioning feature configured to restrain manifold 210.

The illustration of ventilation assembly 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment. In some examples, manifold 210 is not present.

Figure 3:
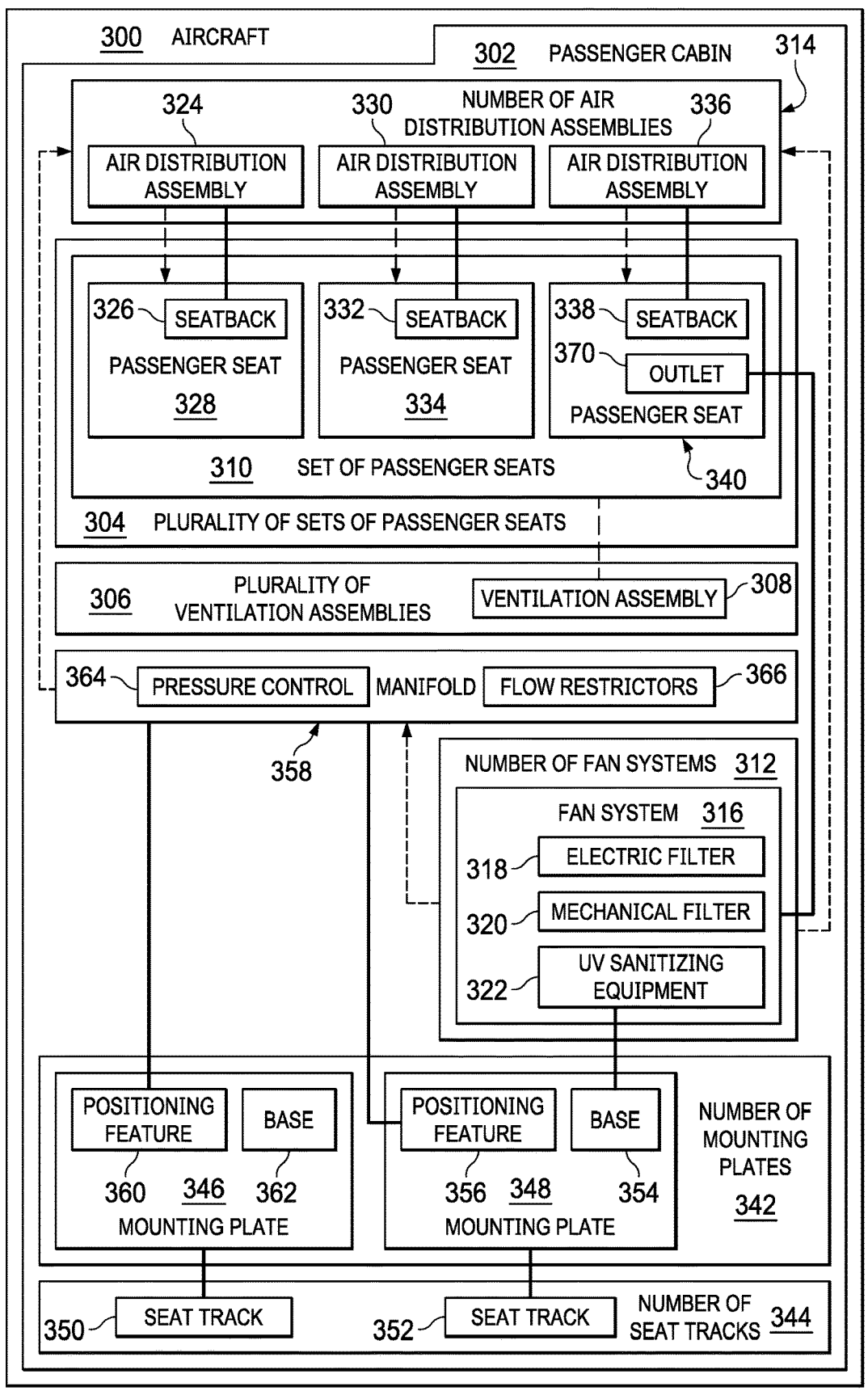
FIG. 3 is a block diagram of an aircraft in accordance with an illustrative embodiment.

Turning now to FIG. 3, a block diagram of an aircraft is depicted in accordance with an illustrative embodiment. In some illustrative examples, aircraft 100 is a physical implementation of aircraft 300.

Ventilation assembly 200 can be implemented in aircraft 300.

Aircraft 300 has passenger cabin 302 with plurality of sets of passenger seats 304. Aircraft 300 comprises plurality of sets of passenger seats 304 and a plurality of ventilation assemblies 306. Each ventilation assembly of plurality of ventilation assemblies 306 is associated with a respective set of passenger seats in plurality of sets of passenger seats 304. Each ventilation assembly of plurality of ventilation assemblies 306 comprises a number of mounting plates, a number of fan systems, and a number of air distribution assemblies.

As depicted, ventilation assembly 308 is associated with set of passenger seats 310. Set of passenger seats 310 is one set in plurality of sets of passenger seats 304. Ventilation assembly 308 comprises number of mounting plates 342, number of fan systems 312, and number of air distribution assemblies 314. Number of fan systems 312 is an example of number of fan systems 202 of FIG. 2. Number of fan systems 312 is configured to draw in and purify air. Number of fan systems 312 provides the purified air to number of air distribution assemblies 314. Number of air distribution assemblies 314 is configured to direct the purified air to passengers within set of passenger seats 310.

As used herein, purified air is air that has a reduced amount of contaminants than air entering number of fan systems 312. Contaminants may include without limitation bacteria or virus elements, as well as dust, mold, and/or other allergens or irritants.

Each fan of number of fan systems 312 comprises at least one of UV sanitizing equipment, an electric filter, or a mechanical air filter. As depicted, fan system 316 is one of number of fan systems 312. Fan system 316 includes at least one of electric filter 318, mechanical filter 320, or UV sanitizing equipment 322. In some illustrative examples, mechanical filter 320 is a high efficiency particulate air filter (HEPA filter).

Each of number of air distribution assemblies 314 can provide laminar flow to create a barrier that minimizes mixing with the ambient environment. For number of air distribution assemblies 314 to deliver purified air, the air supplied to number of air distribution assemblies must be purified. Purified air may be delivered from a purified air source. In this illustrative example, the purified air source is number of fan systems 312.

Mechanical filter 320, such as High efficiency particulate air (HEPA) filters, can be used to purify air flow. High efficiency particulate air (HEPA) filters use pressurized air to flow through the filter. Filter size and material composition of a filter may dictate a pressure required for adequate flow through the filter.

A pressurization source, such as without limitation, a fan, is required to generate the pressurization. In passenger cabin 302, vibration and noise levels created by a motor running the fan, a movement of the fan, and/or by the flow of the air itself, are factors in the design of number of fan systems. It is desirable to maintain vibration and noise levels to within comfortable levels for each individual passenger at each individual seat. It is also desirable to maintain noise levels of all of the fan systems in plurality of ventilation assemblies 306 to within comfortable levels in passenger cabin 302 as a whole. Without limitation, U.S. Occupational Safety and Health Administration Noise standards (29 CFR 1910.95) require employers to have a hearing conservation program in place if workers are exposed to a time-weighted average (TWA) noise level of 85 decibels (dBA) or higher over an 8-hour work shift. Thus, supplying the purified air may utilize number of fan systems 312 that does not require filters of a size or density that require fans of a size and/or power, or airflow at a rate, that creates excessive noise. In some illustrative examples, it may be desirable to keep noise levels at near a passenger seat headrest below 65 decibels.

Further, if fans in number of fan systems 312 are too powerful, they may produce an uncomfortably high velocity of air flow near a passenger. Uncomfortably high velocity of air flow can create a draft. Number of fan systems 312 and manifold 358, when present, can be designed to provide a desired pressure and flow rate of purified air. In some illustrative examples, flow to an air distribution assembly of number of air distribution assemblies is at no more than approximately ten cubic feet per minute.

Additional considerations for number of fan systems 312 includes the power draw and source for a motor driving the fan. Power availability to run number of fan systems 312 is a consideration in choosing the size and type of purification system within a fan system, such as fan system 316. An aircraft environment may not allow for motor weights or power requirements that may be functional in locations such as inside an automobile or in a home or office space.

Ultraviolet purification does not produce a pressure drop, which can allow for smaller and quieter motors that utilize less power than mechanical filter 320 or electric filter 318. UV sanitizing equipment 322 may use more time to purify air within fan system 316. A purification system uses at least one of electric filter 318, mechanical filter 320, or UV sanitizing equipment 322 based on desired pressure and flow rate, available power sources, desired noise threshold, and other considerations.

As depicted, fan system 316 is connected to outlet 370 of passenger seat 340 to receive power. In some illustrative examples, each fan system in number of fan systems 312 is powered by a passenger seat outlet. In some illustrative examples, fan system 316 comprises a female power outlet so that fan system 316 does not prevent passenger use of power from outlet 370.

Each air distribution assembly of number of air distribution assemblies 314 is configured to be removably installed on a seatback of a passenger seat in set of passenger seats 310. As depicted, air distribution assembly 324 is installed on seatback 326 of passenger seat 328. As depicted, air distribution assembly 330 is installed on seatback 332 of passenger seat 334. As depicted, air distribution assembly 336 is installed on seatback 338 of passenger seat 340.

Each mounting plate of number of mounting plates 342 is attached to a respective seat track of number of seat tracks 344 in passenger cabin 302. Each fan system of number of fan systems 312 is positioned beneath a respective set of passenger seats and connected to a base of a respective mounting plate of the number of mounting plates.

Each of number of mounting plates 342 is configured to connect to number of seat tracks 344 without interfering with or interacting with number of passenger seats 304. Number of passenger seats 304 is connected to number of seat tracks 344. Number of mounting plates 342 is connected to number of seat tracks 344. Number of mounting plates 342 is not in contact with number of passenger seats 304. Each of number of mounting plates 342 is configured such that number of fan systems 312 is connected to number of seat tracks 344 without contacting set of passenger seats 310. In some illustrative examples, each of number of mounting plates 342 is configured such that manifold 358 can be restrained without contacting set of passenger seats 310.

Each of number of mounting plates 342 is configured to provide sufficient support and strength to mount a respective fan system and manifold 358 to number of seat tracks 344. At least one of a design of or a material of a respective mounting plate of number of mounting plates 342 is selected to reduce the weight of the respective mounting plate. In some illustrative examples, cavities are present in a respective mounting plate to reduce weight by reducing the amount of material forming the mounting plate.

As depicted, number of mounting plates 342 includes mounting plate 346 and mounting plate 348. Mounting plate 346 is connected to seat track 350 and mounting plate 348 is connected to seat track 352. As depicted, fan system 316 is connected to base 354 of mounting plate 348. By being connected to base 354 of mounting plate 348, fan system 316 is connected to seat track 352. In this illustrative example, number of fan systems 312 only includes one fan system, fan system 316. In other non-depicted illustrative examples, number of fan systems 312 includes more than one fan system. In these illustrative examples, the additional fan systems can be connected to the same or different mounting plates. For example, an additional fan system in number of fan systems 312 could be connected to base 354 of mounting plate 348. In another illustrative example, another fan system in number of fan systems 312 could be connected to base 362 of mounting plate 346.

Further, although only two mounting plates are depicted in number of mounting plates 342, additional mounting plates could be present within number of mounting plates 342. In some illustrative examples, another mounting plate could be connected to seat track 352 and overlapped with mounting plate 348. In another illustrative example, another mounting plate could be connected to seat track 350 and overlapped with mounting plate 346.

Mounting plate 348 also has positioning feature 356. In some illustrative examples, ventilation assembly 308 also includes manifold 358. In some illustrative examples, manifold 358 is optional. Manifold 358 is configured to receive purified air from number of fan systems 312 and equally distribute the purified air to number of air distribution assemblies 314. Manifold 358 is configured to supply air to each air distribution assembly of number of air distribution assemblies 314.

In some illustrative examples, positioning feature 356 restrains manifold 358 within passenger cabin 302. In these illustrative examples, manifold 358 is connected to seat track 352 by mounting plate 348. As depicted, manifold 358 is also restrained within passenger cabin 302 by positioning feature 360. Mounting plate 346 connects manifold 358 to seat track 350.

Manifold 358 is configured to provide pressure control 364 and flow control to each air distribution assembly in number of air distribution assemblies 314. In some illustrative examples, manifold 358 provides flow control through the use of flow restrictors 366.

Manifold 358 comprises flow restrictors configured to substantially equalize pressure and flow rate of the air supplied by manifold 358 to each air distribution assembly.

Each air distribution assembly of the number of air distribution assemblies comprises a pair of air distribution vents, ductwork configured to receive air from at least one fan system of the number of fan systems and direct air to the pair of air distribution vents, and a seat attachment device configured to removably couple the pair of air distribution vents to the seatback such that each air distribution vent is situated on opposite sides of the seatback for providing purified air to a seated passenger.

In some illustrative examples, ventilation assembly 308 provides purified air such that the air breathed by a passenger in a passenger seat in set of passenger seats 310 is substantially the purified air from number of fan systems 312. In some illustrative examples, ventilation assembly 308 provides a large air movement to divert ambient air away from the passenger. In some illustrative examples, ventilation assembly 308 provides air to a passenger without causing the feeling of a draft.

The illustration of passenger cabin 302 in FIG. 3 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, only ventilation assembly 308 is depicted in FIG. 3. Plurality of ventilation assemblies 306 comprises any desirable quantity of ventilation assemblies. Further, each of plurality of ventilation assemblies comprises any desirable quantity of fan systems, any desirable quantity of air distribution assemblies, and any desirable quantity of mounting plates. Additional ventilation assemblies of plurality of ventilation assemblies are not depicted only for ease of explanation.

Further, although manifold 358 is depicted, manifold 358 is optional. Yet further, and as described above, the quantity of air distribution assemblies depicted in number of air distribution assemblies 314, the quantity of fan systems depicted in number of fan systems 312, and the quantity of mounting plates depicted in number of mounting plates 342 are not limiting and can be any desirable quantity based on a design of ventilation assembly 308. In some illustrative examples, each ventilation assembly of plurality of ventilation assemblies 306 has a greater quantity of air distribution assemblies than fan systems.

In some illustrative examples, each air distribution assembly of number of air distribution assemblies 314 is connected to a single fan system of number of fan systems 312.

Figure 4:
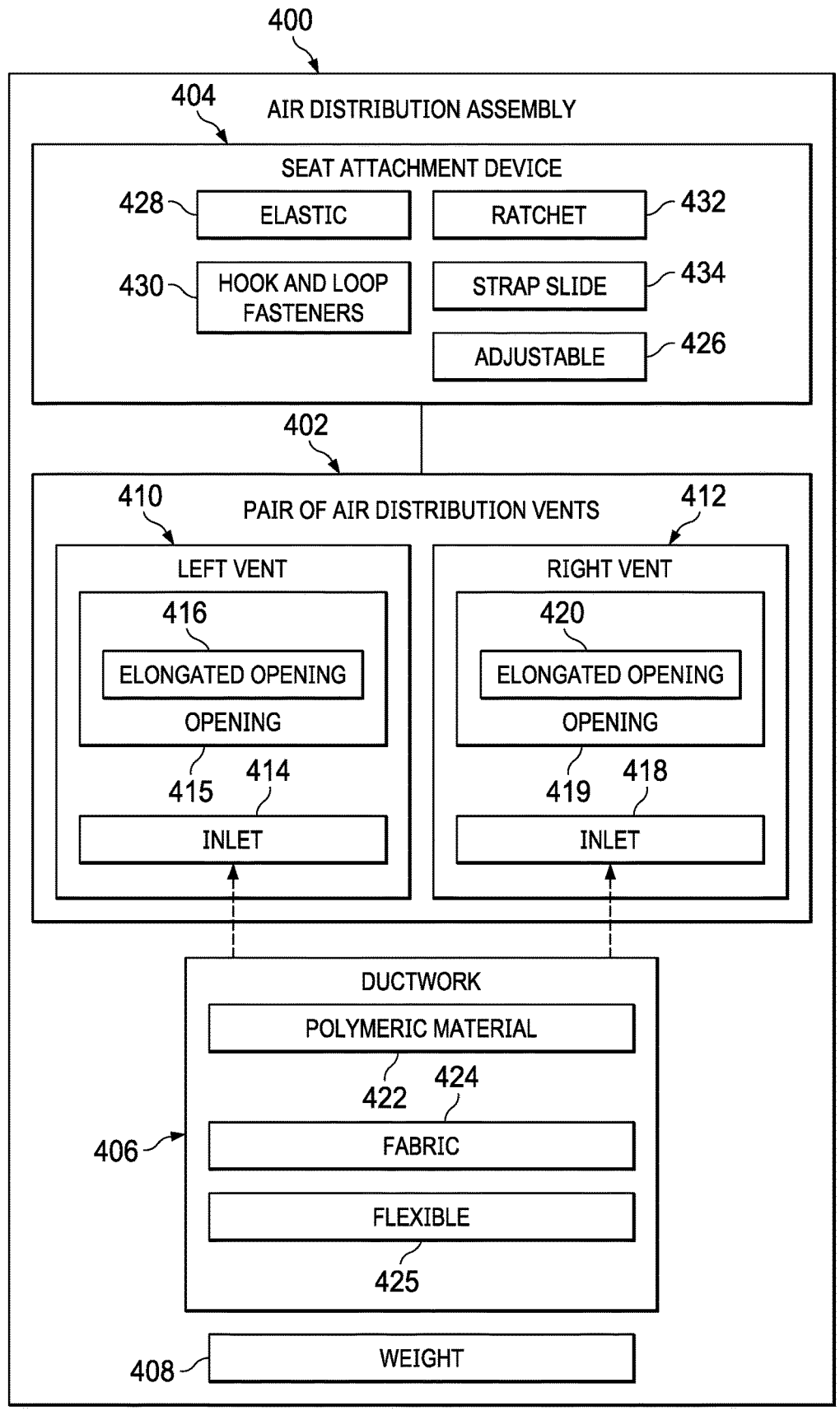
FIG. 4 is a block diagram of an air distribution assembly in accordance with an illustrative embodiment.

Turning now to FIG. 4, a block diagram of an air distribution assembly is depicted in accordance with an illustrative embodiment. Air distribution assembly 400 can be implemented in aircraft 100 of FIG. 1. Air distribution assembly 400 is one of number of air distribution assemblies 204 of FIG. 2. Air distribution assembly 400 is one of number of air distribution assemblies 314 of FIG. 3.

Air distribution assembly 400 is configured to be removably installed on a seatback of a passenger seat. Air distribution assembly comprises pair of air distribution vents 402, seat attachment device 404, and ductwork 406. Seat attachment device 404 is configured to encircle a portion of a seatback to removably couple pair of air distribution vents 402 to the seatback such that each air distribution vent is situated on opposite sides of the seatback for providing purified air to a seated passenger. Seat attachment device 404 is configured to not undesirably interfere with a tray table of a passenger behind the passenger seat. Ductwork 406 is configured to receive air from at least one fan system and direct the air to pair of air distribution vents 402. In some illustrative examples, ductwork 406 is configured to not undesirably interfere with egress from a passenger seat.

To deliver adequate volumes and shapes of air to the passenger's breathing space to displace ambient air, a number of fan systems is configured to provide sufficient air to air distribution assembly 400. Additionally, pair of air distribution vents 402 is configured to deliver adequate volumes and shapes of air to the passenger's breathing space to displace ambient air. In some illustrative examples, pair of air distribution vents 402 have a design configured to provide laminar streams of air. The embodiments shown provide delivery of purified air that approaches the effectiveness provided by a face mask on a passenger, without the need to wear any mask.

Pair of air distribution vents 402 is formed of any desirable material. In some illustrative examples, pair of air distribution vents 402 is formed of a polymeric material. In some illustrative examples, pair of air distribution vents 402 is formed of a rigid material. In some illustrative examples, pair of air distribution vents 402 is formed at least partially of a flexible material.

Pair of air distribution vents 402 includes left vent 410 and right vent 412. Each air distribution vent comprises an inlet and an opening. Left vent 410 has inlet 414 connected to ductwork 406 and opening 415. In some illustrative examples, opening 415 takes the form of elongated opening 416. When opening 415 takes the form of elongated opening 416, left vent 410 can be referred to as a blade vent. Opening 415 is configured to provide an airflow to a passenger in the passenger seat having air distribution assembly 400.

Right vent 412 has inlet 418 connected to ductwork 406 and opening 419. In some illustrative examples, opening 419 takes the form of elongated opening 420. When opening 419 takes the form of elongated opening 420, right vent 412 can be referred to as a blade vent. Opening 419 is configured to provide an airflow to a passenger in the passenger seat having air distribution assembly 400.

Ductwork 406 is configured to connect to inlet 414 and inlet 418 to send purified air from a number of fan systems to left vent 410 and right vent 412. Ductwork 406 includes any desirable quantity of ducts. Ductwork 406 has any desirable physical characteristics. In some illustrative examples, ductwork 406 is flexible 425. When ductwork 406 is flexible 425, ductwork 406 can move in response to reclining a seatback. In some illustrative examples, ductwork 406 is formed of polymeric material 422. In some illustrative examples, ductwork 406 is formed of fabric 424. Material selections for ductwork 406 can be based on at least one of cost, manufacturability, or weight.

Seat attachment device 404 is adjustable 426 to allow for securing seat attachment device 404 onto a seatback. In some illustrative examples, seat attachment device 404 is adjustable 426 to fit seatbacks of different sizes.

Seat attachment device 404 comprises one of elastic 428, hook and look fasteners 430, ratchet 432, or strap slide 434. When seat attachment device 404 comprises elastic 428, seat attachment device 404 is expandable to be placed around a seatback. In some illustrative examples, seat attachment device 404 is an expandable fabric sleeve comprising elastic 428.

In some illustrative examples, hook and loop fasteners 430 are connected directly to number of air distribution vents 402. In these illustrative examples, hook and loop fasteners 430 are also directly connected to the seatback.

In some illustrative examples, hook and loop fasteners 430 are indirectly connected to number of air distribution vents 402. In these illustrative examples, an intermediate component is directly connected to number of air distribution vents 402 and is also directly connected to hook and loop fasteners 430. In these illustrative examples, at least one dimension of the intermediate component of seat attachment device 404 is adjusted through the use of hook and loop fasteners 430. In some of these illustrative examples, a length of the intermediate component of seat attachment device 404 is adjusted through the use of hook and loop fasteners 430.

Weight 408 of air distribution assembly 400 is below a threshold weight for recertification of the passenger seat. The threshold weight is a set weight either by value or by percentage of weight of passenger seat over which the passenger seat will have to be recertified. By weight 408 being below the threshold weight, air distribution assembly 400 can be attached to the passenger seat without recertifying the seat.

Air distribution assembly 400 is configured such that when air distribution assembly 400 is installed on the seatback of a passenger seat, airflows from pair of air distribution vents 402 converge and blend in front of a nose and mouth of a passenger to form a personal breathing space that envelopes an inhalation sphere, impeding transgression of ambient air from crossing through the respective barriers and entering into the personal breathing space, such that the inhalation sphere comprises purified air supplied to air distribution assembly 400 by a number of fan systems such that air inhaled by the passenger comes from the inhalation sphere. Air distribution assembly 400 is configured to provide airflows from pair of air distribution vents 402 that converge and blend by configuring the respective shapes of elongated opening 416 and elongated opening 420. Air distribution assembly 400 is configured to provide airflows from pair of air distribution vents 402 that converge and blend by configuring the positions of left vent 410 and right vent 412 in air distribution assembly 400.

Figure 5:
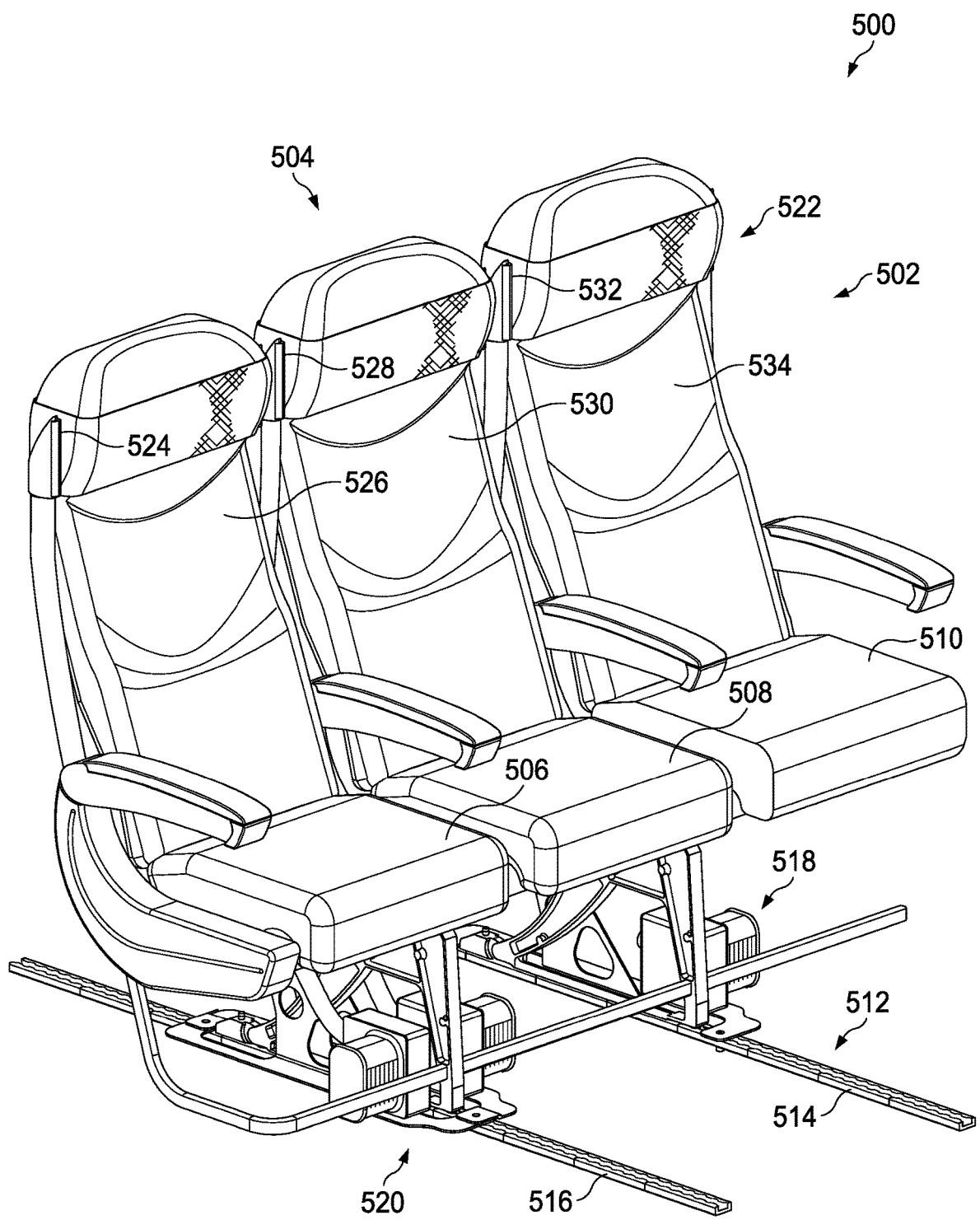
FIG. 5 is a front isometric view of a set of passenger seats and a ventilation assembly in accordance with an illustrative embodiment.

Turning now to FIG. 5, a front isometric view of a set of passenger seats and a ventilation assembly is depicted in accordance with an illustrative embodiment. Set of passenger seats 502 is present within passenger cabin 500. Set of passenger seats 502 is a physical implementation of set of passenger seats 310 of FIG. 3. In this illustrative example, set of passenger seats 502 can also be referred to as a row of passenger seats.

Ventilation assembly 504 is associated with set of passenger seats 502. Passenger seat 506, passenger seat 508, and passenger seat 510 are all connected to set of seat tracks 512. Set of seat tracks 512 includes seat track 514 and seat track 516.

Ventilation assembly 504 includes number of fan systems 518, number of mounting plates 520, and number of air distribution assemblies 522. Number of mounting plates 520 connects number of fan systems 518 to set of seat tracks 512. Number of fan systems 518 and number of mounting plates 520 are not in contact with set of passenger seats 502. As depicted, number of air distribution assemblies 522 includes air distribution assembly 524 attached to seatback 526 of passenger seat 506, air distribution assembly 528 attached to seatback 530 of passenger seat 508, and air distribution assembly 532 attached to seatback 534 of passenger seat 510.

Figure 6:
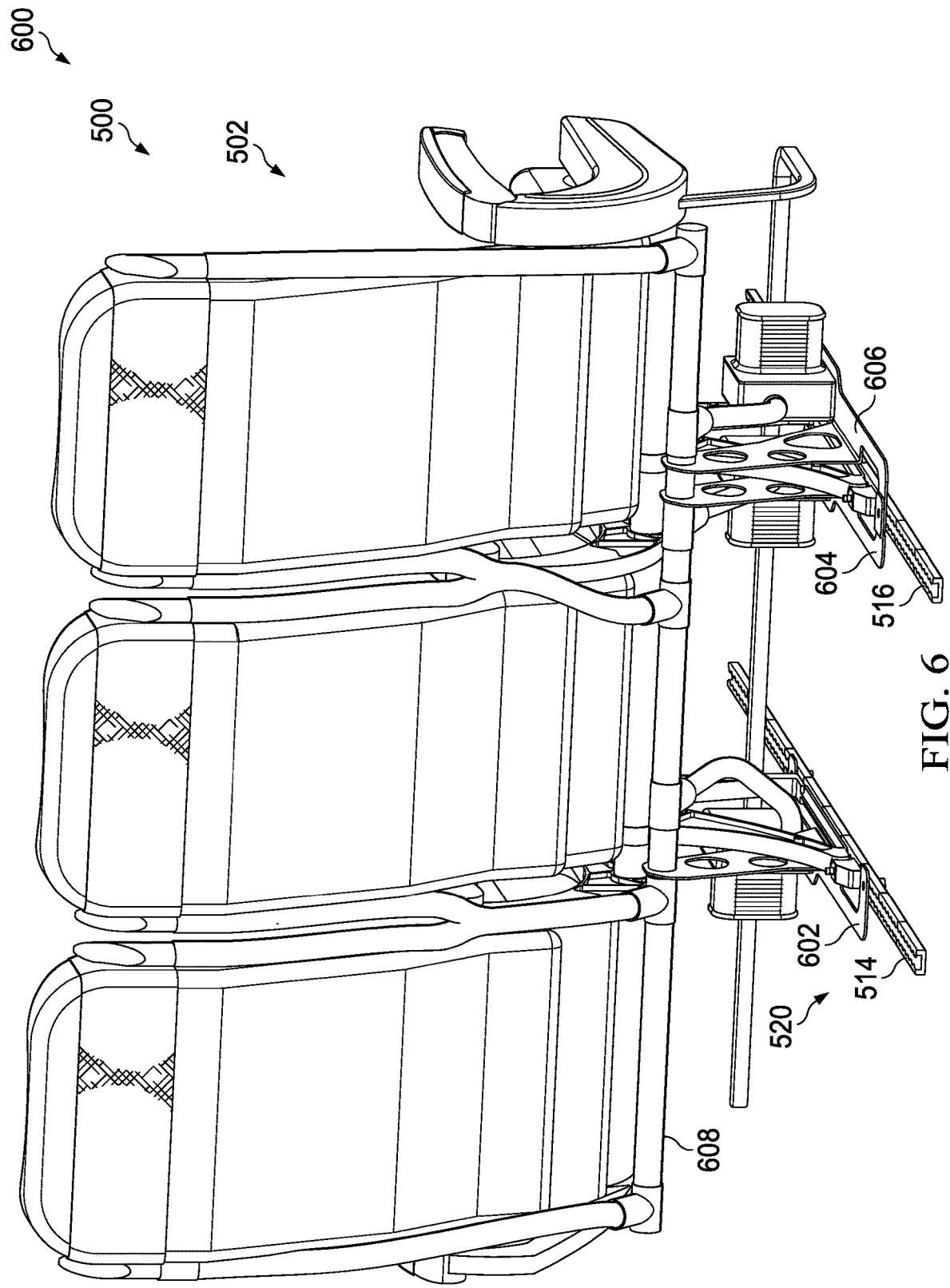
FIG. 6 is a back isometric view of a set of passenger seats and a ventilation assembly in accordance with an illustrative embodiment.

Turning now to FIG. 6, a back isometric view of a set of passenger seats and a ventilation assembly is depicted in accordance with an illustrative embodiment. View 600 is a view within passenger cabin 500. View 600 is a back view of a portion of set of passenger seats 502.

Mounting plate 602 of number of mounting plates 520 is connected to seat track 514. Mounting plate 604 and mounting plate 606 of number of mounting plates 520 are connected to seat track 516.

Manifold 608 connects number of fan systems 518 to number of air distribution assemblies 522. Manifold 608 distributes purified air from number of fan systems 518 to ductwork of number of air distribution assemblies 522.

Manifold 608 is not connected to set of passenger seats 502. Each of number of mounting plates 520 restrains manifold 608 within passenger cabin 500. Each of number of mounting plates 520 connects manifold 608 to number of seat tracks 512. As depicted, manifold 608 extends through a respective positioning feature of each of mounting plate 602, mounting plate 604, and mounting plate 606.

Figure 7:
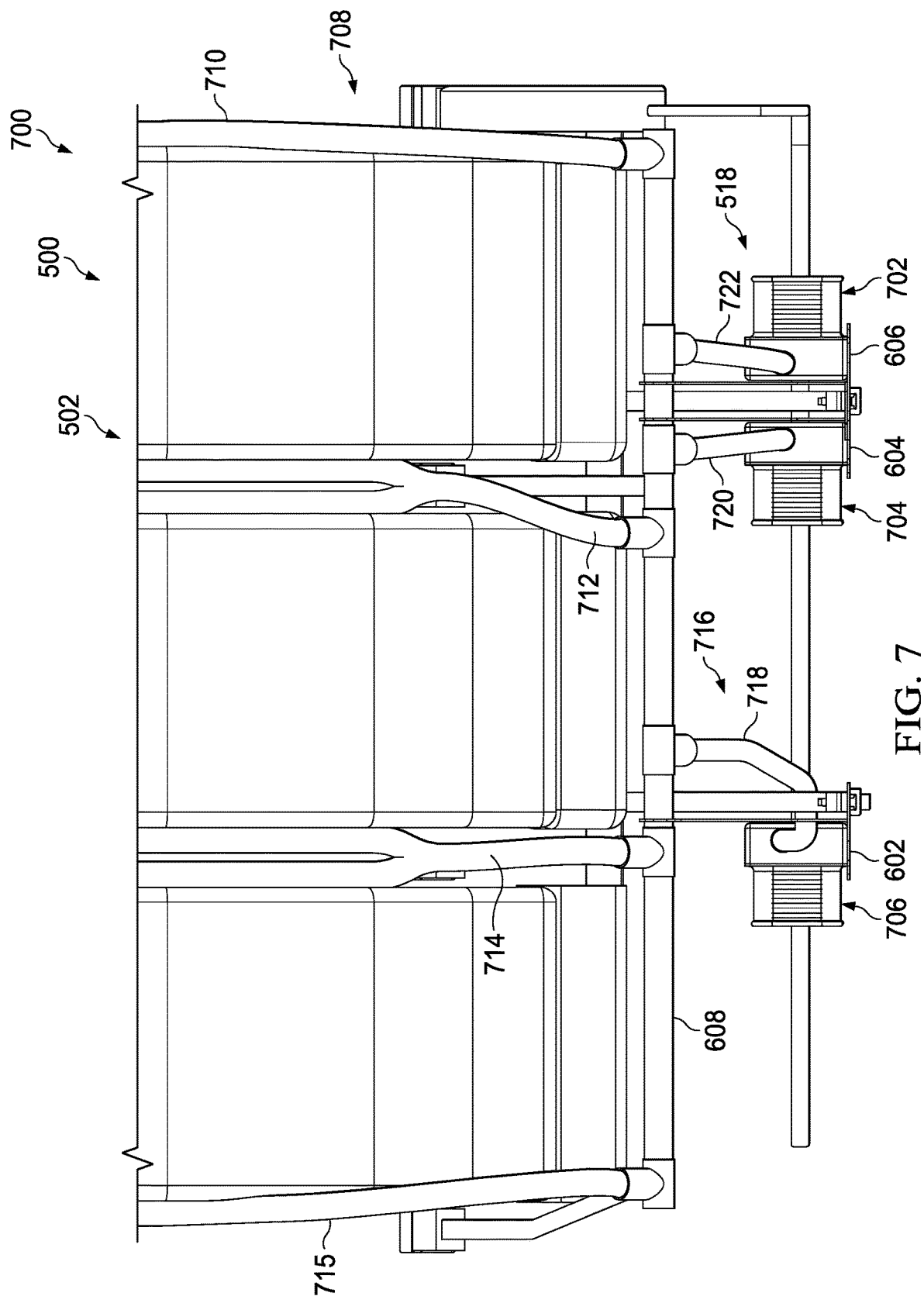
FIG. 7 is a back view of a set of passenger seats and a ventilation assembly in accordance with an illustrative embodiment.

Turning now to FIG. 7, a back view of a set of passenger seats and a ventilation assembly is depicted in accordance with an illustrative embodiment. View 700 is a view of the bottom of set of passenger seats 502 within passenger cabin 500. In view 700, each of number of fan systems 518 is visible. Number of fan systems 518 includes fan system 702, fan system 704, and fan system 706.

Number of air distribution assemblies 522 includes ductwork 708 that connects to manifold 608. In some illustrative examples, ductwork 706 is configured to not undesirably interfere with egress from any of the passenger seats in set of passenger seats 502. Material for ductwork 708 is selected to provide airflow to number of air distribution assemblies 522. Material for ductwork 708 is selected based on weight. Duct 710 connects manifold 608 to air distribution assembly 524. Ducts 712 connect manifold 608 to air distribution assembly 524 and air distribution assembly 528. Ducts 712 are designed to provide air to air distribution assembly 524 and air distribution assembly 528 without undesirably obstructing movement of passenger seat 506 or passenger seat 508. Ducts 714 connect manifold 608 to air distribution assembly 528 and air distribution assembly 532. Ducts 714 are designed to provide air to air distribution assembly 528 and air distribution assembly 532 without undesirably obstructing movement of passenger seat 508 or passenger seat 510. Duct 715 connects manifold 608 to air distribution assembly 532.

Ductwork 716 connects number of fan systems 518 to manifold 608. Duct 718 connects fan system 706 to manifold 608. Duct 720 connects fan system 704 to manifold 608. Duct 722 connects fan system 702 to manifold 608. In some illustrative examples, ductwork 716 is configured to not undesirably interfere with egress from any of the passenger seats in set of passenger seats 502.

As depicted, number of fan systems 518 provides purified air to manifold 608. Manifold 608 distributes the air to ductwork 708. Ductwork 708 directs the purified air upward to number of air distribution assemblies 522 of FIG. 5.

Figure 8:
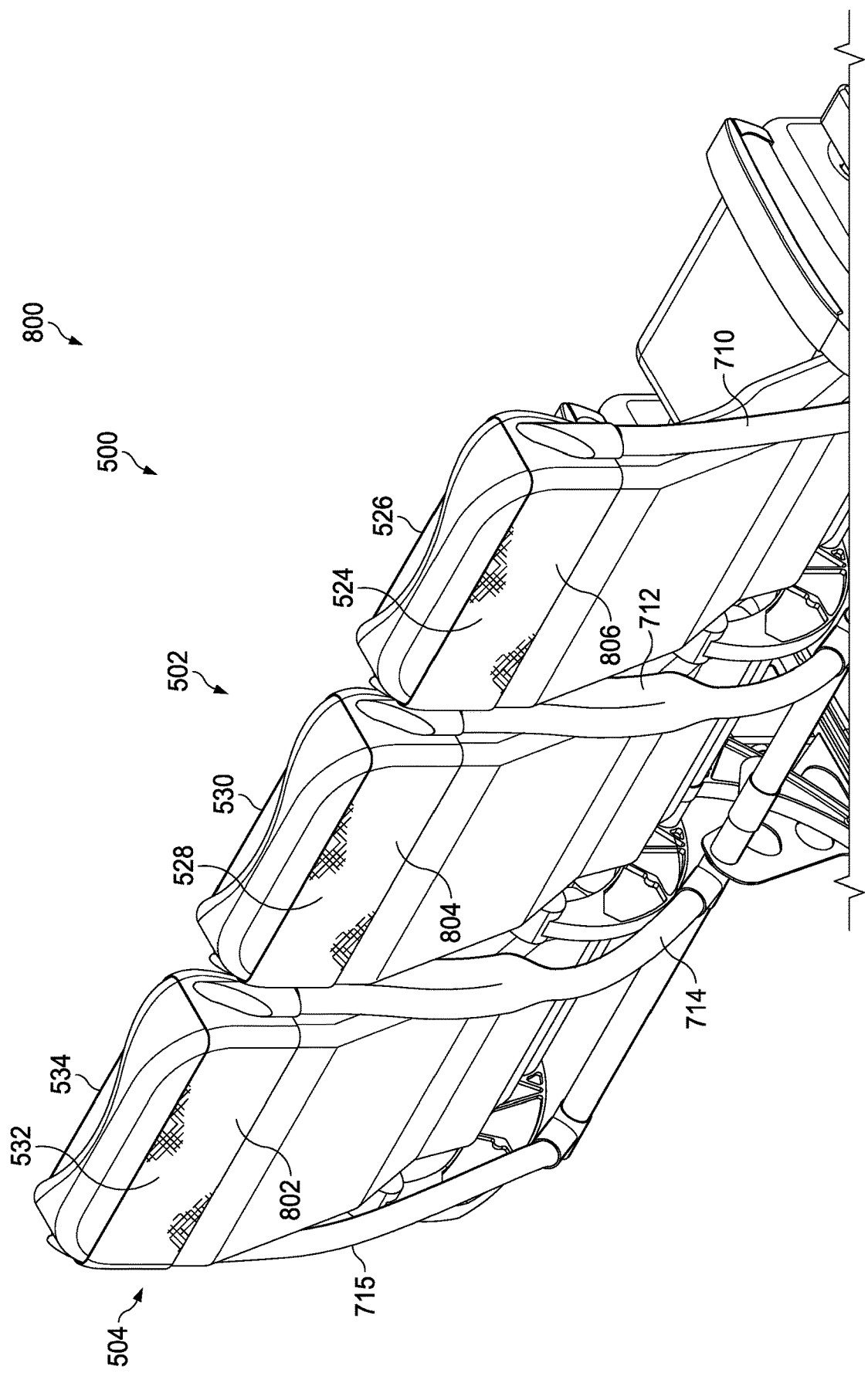
FIG. 8 is a back isometric view of a set of passenger seats and a ventilation assembly in accordance with an illustrative embodiment.

Turning now to FIG. 8, a back isometric view of a set of passenger seats and a ventilation assembly is depicted in accordance with an illustrative embodiment. View 800 is a view of set of passenger seats 502 within passenger cabin 500. In view 800, a seat attachment device of each air distribution assembly in number of air distribution assemblies 522 is visible. Seat attachment device 802 connects air distribution assembly 532 to seatback 534. Seat attachment device 804 connects air distribution assembly 528 to seatback 530. Seat attachment device 806 connects air distribution assembly 524 to seatback 526. As depicted, each of seat attachment device 802, seat attachment device 804, and seat attachment device 806 is an expandable fabric sleeve.

Although each seat attachment device is depicted at a respective headrest of a passenger seat, in some illustrative examples, at least air distribution assembly of number of air distribution assemblies 522 can be at a different height on a respective seatback. In some illustrative examples, ductwork 708 is flexible and any of seat attachment device 802, seat attachment device 804, or seat attachment device 806 can be lowered along a respective seatback to position the respective air distribution assembly relative to a head of a passenger.

Figure 9:
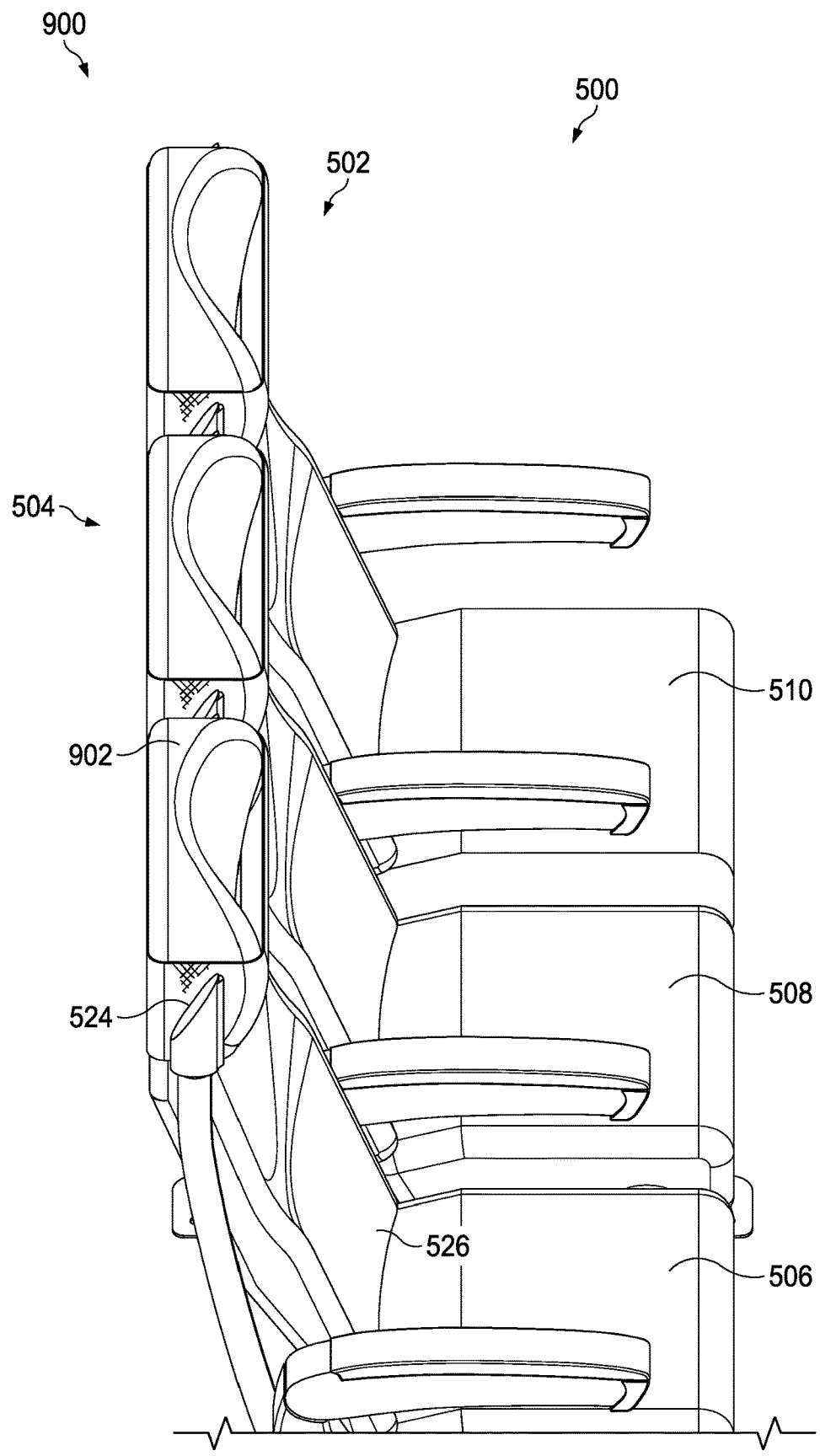
FIG. 9 is an elevated side view of a set of passenger seats and a ventilation assembly in accordance with an illustrative embodiment.

Turning now to FIG. 9, an elevated side view of a set of passenger seats and a ventilation assembly is depicted in accordance with an illustrative embodiment. View 900 is a view of set of passenger seats 502 within passenger cabin 500.

As can be seen in view 900, air distribution assembly 524 attached to passenger seat 506 does not obstruct entry into or exit from set of passenger seats 502. Air distribution assembly 524 is connected to headrest 902 of passenger seat 506. As depicted, vents of air distribution assembly 524 do not extend past headrest 902 into a passenger space of passenger seat 506. Ventilation assembly 504 does not intrude into passenger spaces of set of passenger seats 502. Ventilation assembly 504 provides purified air to personal breathing areas for passengers in set of passenger seats 502.

Figure 10:
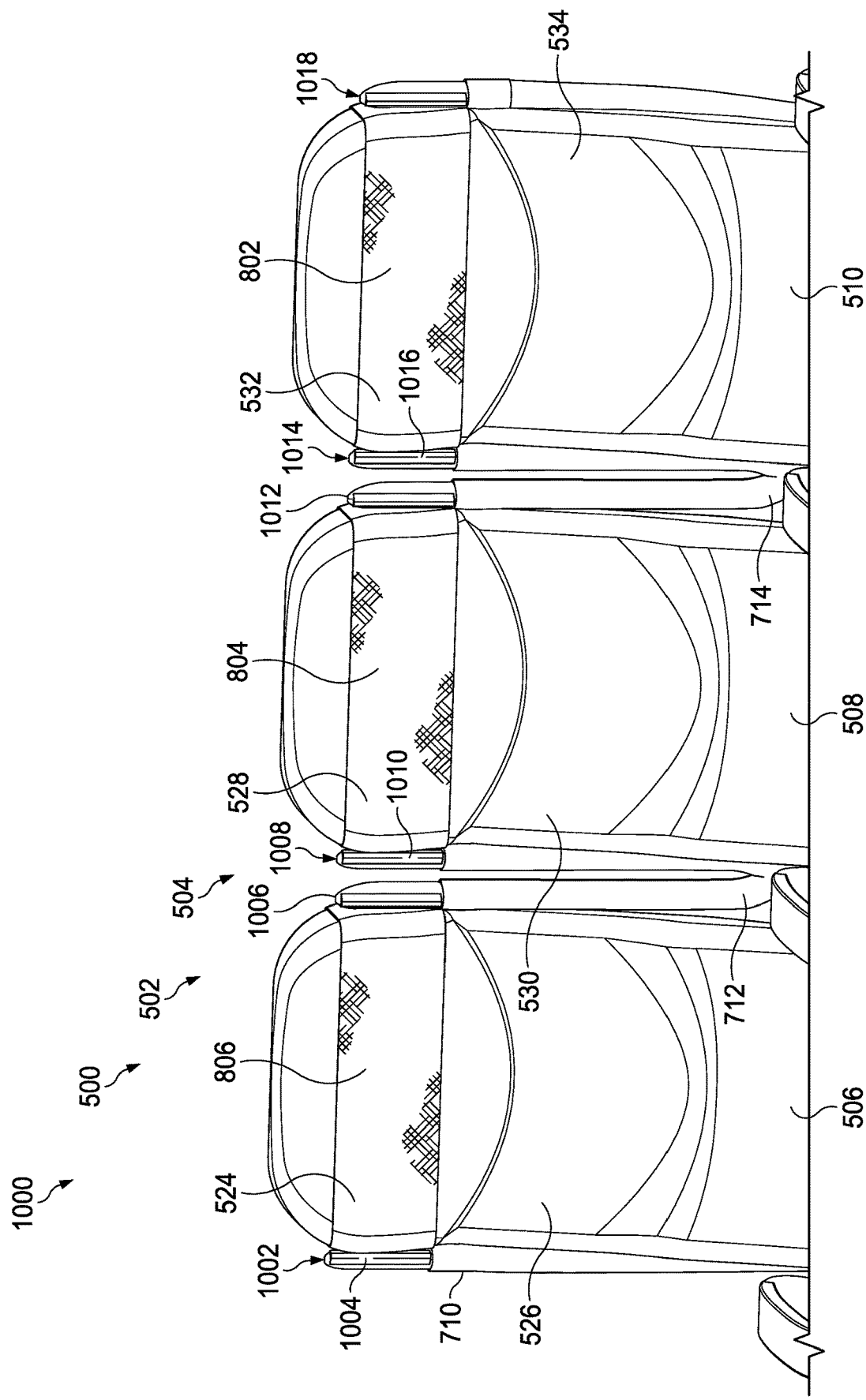
FIG. 10 is a front view of a set of passenger seats and a ventilation assembly in accordance with an illustrative embodiment.

Turning now to FIG. 10, a front view of a set of passenger seats and a ventilation assembly is depicted in accordance with an illustrative embodiment. View 1000 is a front view of set of passenger seats 502 within passenger cabin 500.

Each air distribution assembly of ventilation assembly 504 is configured to be removably installed on a seatback of a passenger seat. Each air distribution assembly comprises a pair of air distribution vents, a seat attachment device configured to encircle a portion of the seatback to removably couple the pair of air distribution vents to the seatback such that each air distribution vent is situated on opposite sides of the seatback for providing purified air to a seated passenger, and ductwork configured to receive air from at least one fan system and direct the air to the pair of air distribution vents.

Air distribution assembly 524 is configured to be removably installed on seatback 526 of passenger seat 506. Air distribution assembly 524 comprises pair of air distribution vents 1002, seat attachment device 806, and ductwork, duct 710 and ducts 712. Seat attachment device 806 is configured to encircle a portion of seatback 526 to removably couple pair of air distribution vents 1002 to seatback 526 such that each air distribution vent is situated on opposite sides of seatback 526 for providing purified air to a seated passenger. For example, left vent 1004 is on an opposite side of seatback 526 from right vent 1006. Ductwork, duct 710 and ducts 712, is configured to receive air from at least one fan system, such as fan system 702, fan system 704, or fan system 706 of FIG. 7, and direct the air to pair of air distribution vents 1002.

Seat attachment device 806 takes any desirable form. In FIGS. 5-13, seat attachment device 806 takes the form of an elastic sleeve. The elastic sleeve expands to encircle headrest 902 of passenger seat 506 and contracts to hold pair of air distribution vents 1002 in place against headrest 902.

Air distribution assembly 528 is configured to be removably installed on seatback 530 of passenger seat 508. Air distribution assembly 528 comprises pair of air distribution vents 1008, seat attachment device 804, and ductwork, ducts 712 and ducts 714. Seat attachment device 804 is configured to encircle a portion of seatback 530 to removably couple pair of air distribution vents 1008 to seatback 530 such that each air distribution vent is situated on opposite sides of seatback 530 for providing purified air to a seated passenger. For example, left vent 1010 is on an opposite side of seatback 530 from right vent 1012. Ductwork, ducts 712 and ducts 714, is configured to receive air from at least one fan system, such as fan system 702, fan system 704, or fan system 706 of FIG. 7, and direct the air to pair of air distribution vents 1008.

Seat attachment device 804 takes any desirable form. In FIGS. 5-13, seat attachment device 804 takes the form of an elastic sleeve. The elastic sleeve expands to encircle a headrest of passenger seat 508 and contracts to hold pair of air distribution vents 1008 in place against the headrest.

Air distribution assembly 532 is configured to be removably installed on seatback 534 of passenger seat 510. Air distribution assembly 532 comprises pair of air distribution vents 1014, seat attachment device 802, and ductwork, ducts 714 and duct 715. Seat attachment device 802 is configured to encircle a portion of seatback 534 to removably couple pair of air distribution vents 1014 to seatback 534 such that each air distribution vent is situated on opposite sides of seatback 534 for providing purified air to a seated passenger. For example, left vent 1016 is on an opposite side of seatback 534 from right vent 1018. Ductwork, ducts 714 and duct 715, is configured to receive air from at least one fan system, such as fan system 702, fan system 704, or fan system 706 of FIG. 7, and direct the air to pair of air distribution vents 1014.

Seat attachment device 802 takes any desirable form. In FIGS. 5-13, seat attachment device 802 takes the form of an elastic sleeve. The elastic sleeve expands to encircle a headrest of passenger seat 510 and contracts to hold pair of air distribution vents 1014 in place against the headrest.

Figure 11:
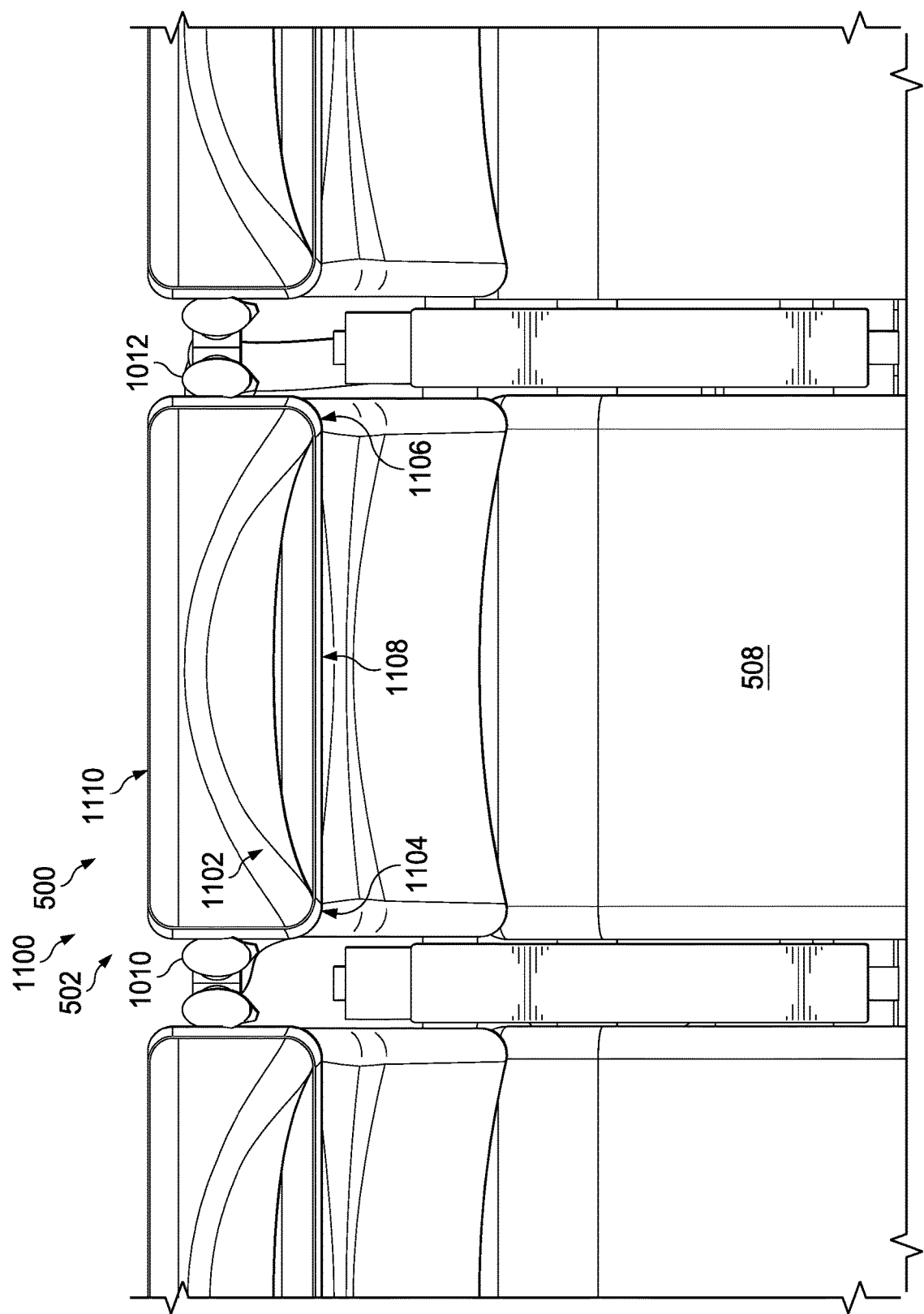
FIG. 11 is a top view of a set of passenger seats and a ventilation assembly in accordance with an illustrative embodiment.

Turning now to FIG. 11, a top view of a set of passenger seats and a ventilation assembly is depicted in accordance with an illustrative embodiment. View 1100 is a top view of set of passenger seats 502 within passenger cabin 500.

In view 1100, boundaries of headrest 1102 of passenger seat 508 are seen. Headrest 1102 has leading edge 1104 and leading edge 1106. Leading edge boundary 1108 is an innermost position for a portion of headrest 1102 into passenger seat 508. Trailing edge boundary 1110 is an outermost position for a portion of headrest 1102 on the back of passenger seat 508.

As depicted, left vent 1010 and right vent 1012 are mounted between leading edge boundary 1108 and trailing edge boundary 1110. As depicted, left vent 1010 and right vent 1012 do not extend past leading edge boundary 1108. A passenger seated in passenger seat 508 will not inadvertently contact left vent 1010 or right vent 1012. By left vent 1010 and right vent 1012 being positioned behind leading edge boundary 1108, left vent 1010 and right vent 1012 do not interfere with entrance or exit from set of passenger seats 502. By left vent 1010 and right vent 1012 being positioned behind leading edge boundary 1108, left vent 1010 and right vent 1012 do not impact a passenger within passenger seat 508.

Figure 12:
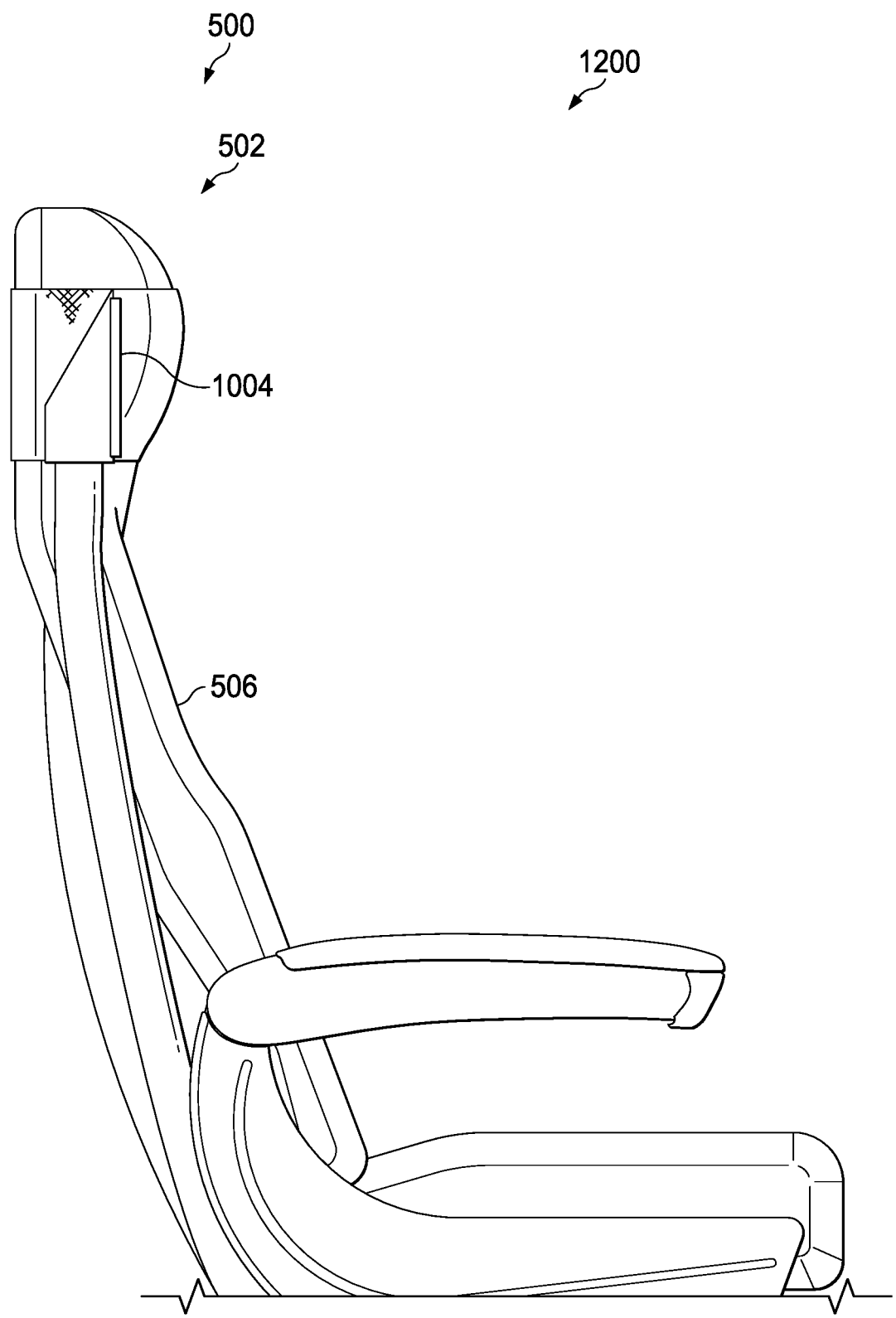
FIG. 12 is a side view of a set of passenger seats and a ventilation assembly in accordance with an illustrative embodiment.

Turning now to FIG. 12, a side view of a set of passenger seats and a ventilation assembly is depicted in accordance with an illustrative embodiment. View 1200 is a side view of set of passenger seats 502 within passenger cabin 500. As can be seen in view 1200, left vent 1004 does not extend past leading edge boundary 1108. Additionally, each vent of air distribution assembly 524, air distribution assembly 528, and air distribution assembly 532 do not extend past a respective leading-edge boundary of a respective passenger seat. For example, pair of air distribution vents 1002 do not extend past a respective leading-edge boundary of passenger seat 506. Also, pair of air distribution vents 1014 do not extend past a respective leading-edge boundary of passenger seat 510.

Figure 13:
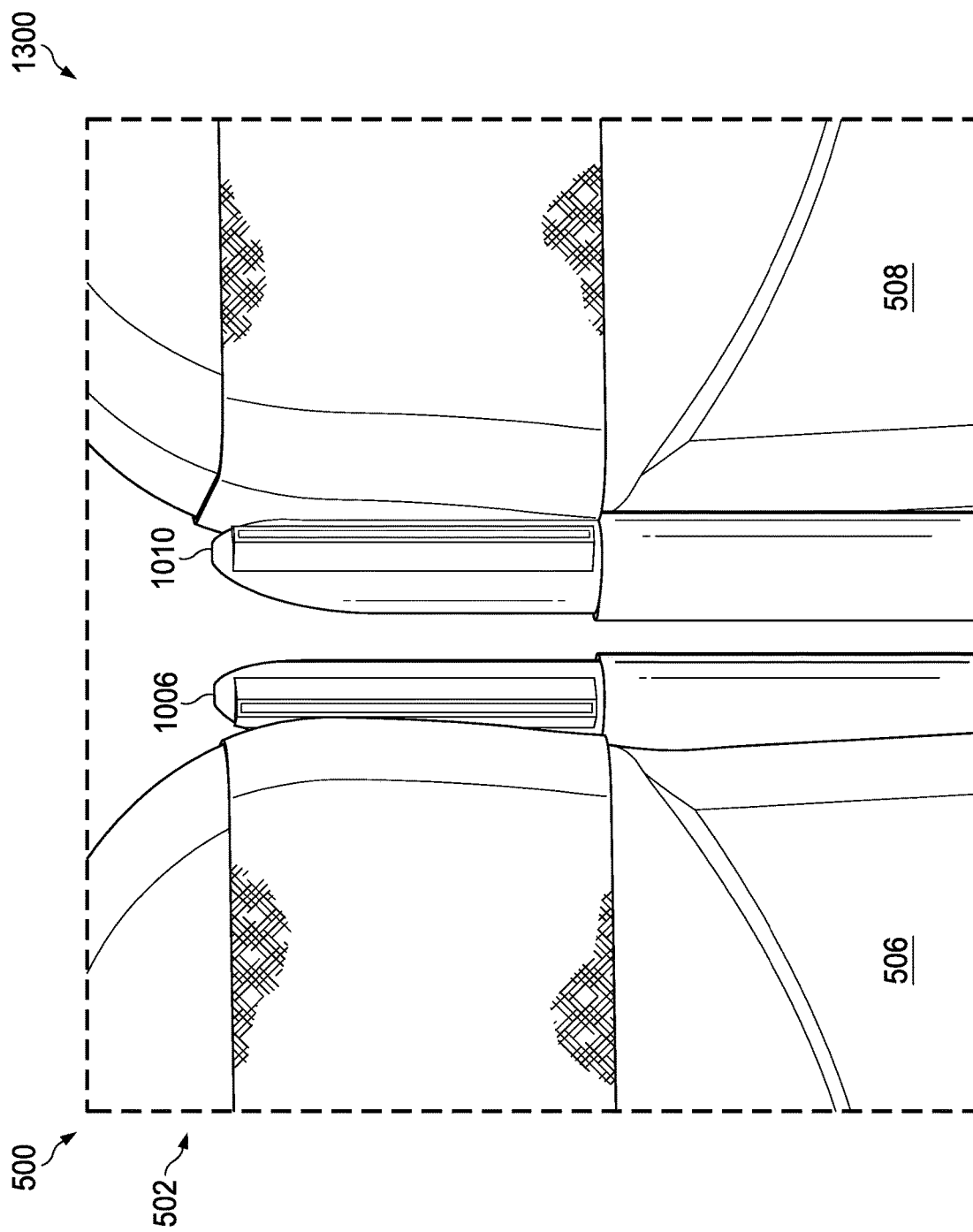
FIG. 13 is a front view of air distribution vents attached to adjacent passenger seats in accordance with an illustrative embodiment.

Turning now to FIG. 13, a front view of air distribution vents attached to adjacent passenger seats is depicted in accordance with an illustrative embodiment. View 1300 is a view of right vent 1006 and left vent 1010 within passenger cabin 500.

In view 1300, a gap is present between right vent 1006 and left vent 1010. As can be seen, right vent 1006 and left vent 1010 can pass by each other should passenger seat 506 or passenger seat 508 be reclined.

The illustration of ventilation assembly 504 associated with set of passenger seats 502 in FIGS. 5-13 is not meant to imply physical or architectural limitations to the manner in which an illustrative embodiment may be implemented. Other components in addition to or in place of the ones illustrated may be used. Some components may be unnecessary.

For example, there could be any desirable quantity of fan systems in number of fan systems 518. In some illustrative examples, manifold 608 is optional. The quantity of inlets and quantity of outlets in manifold 608 can be different than depicted in FIGS. 5-13 to accommodate the quantity of air distribution assemblies, the quantity of ducts, and the quantity of fan systems provided.

As depicted, each of seat attachment device 802, seat attachment device 804, and seat attachment device 806 is an expandable fabric sleeve. In some illustrative examples, any of seat attachment device 802, seat attachment device 804, and seat attachment device 806 can have a different design, such as a slipcover that covers at least a portion of the top of a head rest, a ratcheted belt, a strap slide, or other desirable design. A slipcover that covers at least a portion of the top of a head rest could be used as a seat attachment device that indexes the height of the air distribution device to a set height on the respective passenger seat. In these illustrative examples, the portion of the slipcover that covers a portion of the head rest limits the movement of the slipcover downward.

As yet another example, any of the seat attachment devices can be moved along a respective seatback to desirably position a respective air distribution assembly based on a height of a passenger. For example, one of number of air distribution assemblies 522 can be slid downward to position the respective air distribution assembly for a child.

In other illustrative examples, more than one air distribution assembly is associated with a passenger seat. In some illustrative examples, a first air distribution assembly is positioned for an adult height and a second air distribution assembly is positioned on the same passenger seat for a child's height.

In some illustrative examples, set of passenger seats 502 can include more or fewer passenger seats than three passenger seats. Although set of passenger seats 502 is a row of passenger seats, a set of passenger seats can have less than a full row of passenger seats. In some illustrative examples, set of passenger seats 502 is a single seat, such as passenger seat 506. In some illustrative examples, set of passenger seats 502 includes seats from more than one row of passenger seats.

Additionally, although ductwork 708 is shown as flexible, in some illustrative examples, ductwork 708 can be rigid. As depicted, ductwork 708 includes ducts 712 that provide air to more than one air distribution assembly. In some non-depicted examples, ductwork 708 includes only ducts that provide air to a single air distribution assembly.

Figure 14:
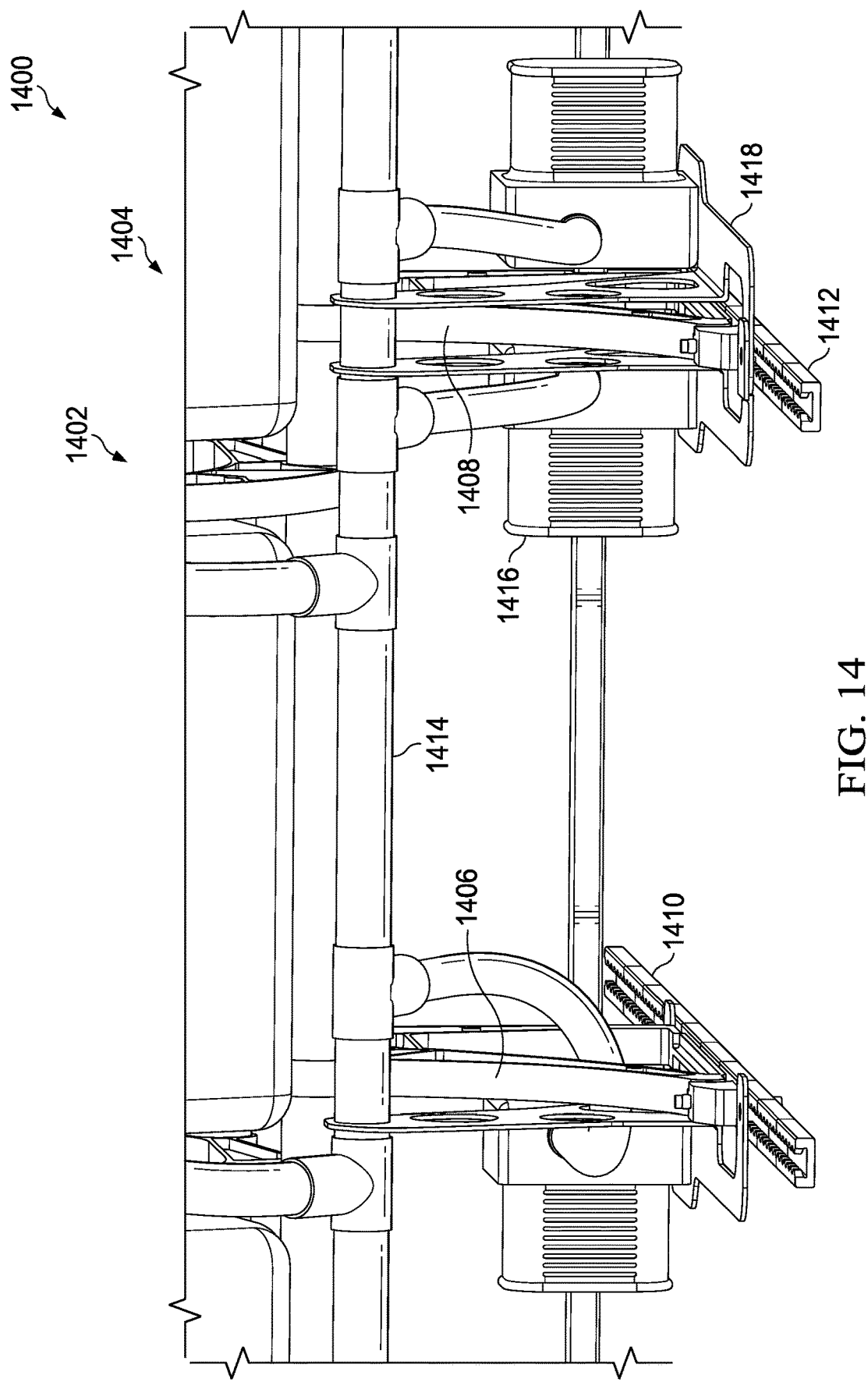
FIG. 14 is an isometric back view of a ventilation assembly in accordance with an illustrative embodiment.

Turning now to FIG. 14, an isometric back view of a ventilation assembly is depicted in accordance with an illustrative embodiment. Ventilation assembly 1402 in view 1400 is a physical implementation of ventilation assembly 200 of FIG. 2. Ventilation assembly 1402 in view 1400 is a physical implementation of ventilation assembly 308 of FIG. 3.

Ventilation assembly 1402 is associated with set of passenger seats 1404. Leg 1406 and leg 1408 mount set of passenger seats 1404 to number of seat tracks, seat track 1410 and seat track 1412. Manifold 1414 and number of fan systems 1416 are mounted to seat track 1410 and seat track 1412 independently of set of passenger seats 1404. Manifold 1414 and number of fan systems 1416 are mounted to seat track 1410 and seat track 1412 by number of mounting plates 1418.

Figure 15:
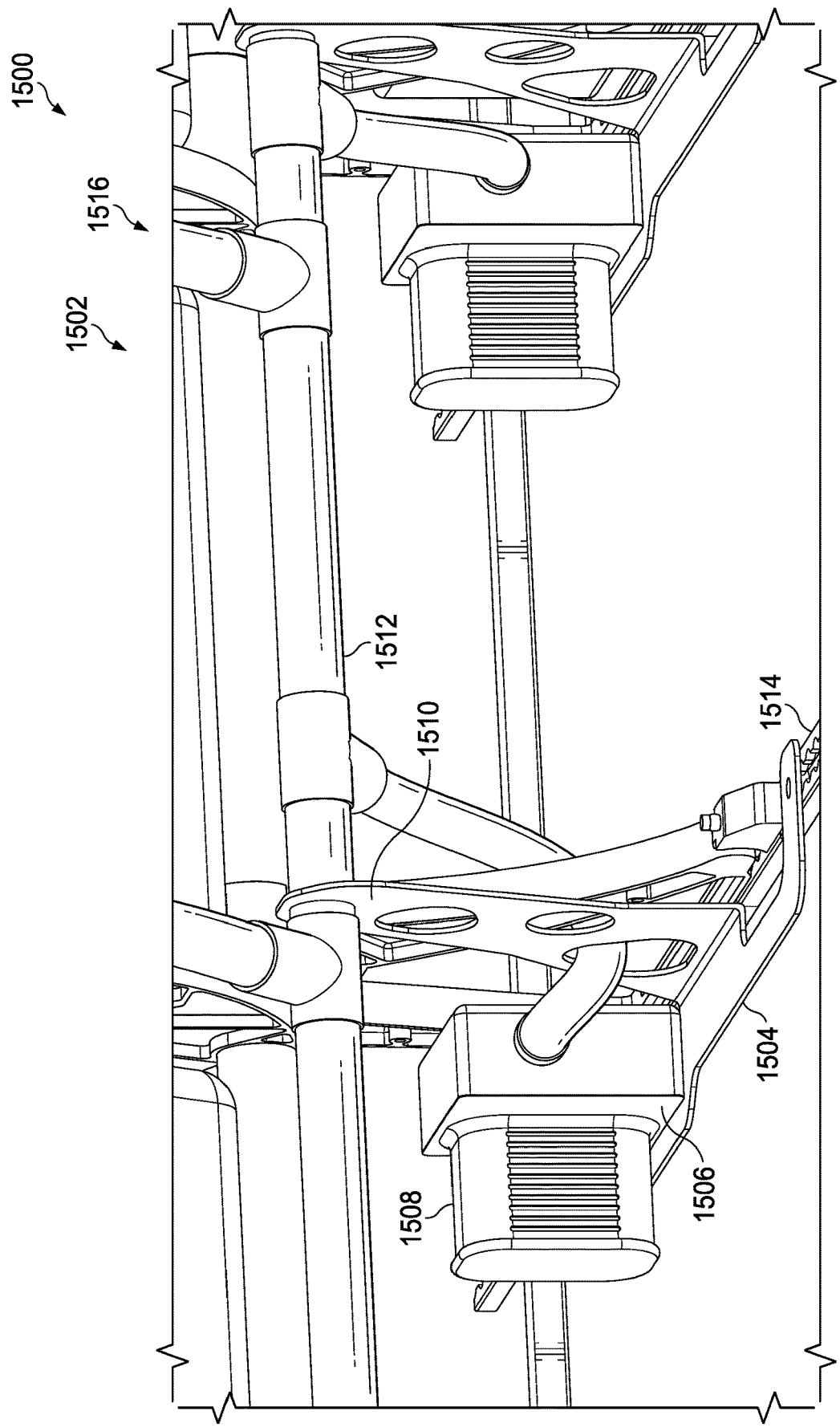
FIG. 15 is an isometric back view of a ventilation assembly in accordance with an illustrative embodiment.

Turning now to FIG. 15, an isometric back view of a ventilation assembly is depicted in accordance with an illustrative embodiment. Ventilation assembly 1502 in view 1500 is a physical implementation of ventilation assembly 200 of FIG. 2. Ventilation assembly 1502 in view 1500 is a physical implementation of ventilation assembly 308 of FIG. 3. Ventilation assembly 1502 includes mounting plate 1504 with base 1506 and positioning feature 1510. Base 1506 is configured to be connected to fan system 1508. As depicted, fan system 1508 is connected to seat track 1514 by mounting plate 1504.

Positioning feature 1510 is configured to restrain manifold 1512 within passenger cabin 1516. Mounting plate 1504 connects manifold 1512 to seat track 1514 in passenger cabin 1516. As depicted, manifold 1512 extends through positioning feature 1510 of mounting plate 1504.

Figure 16:
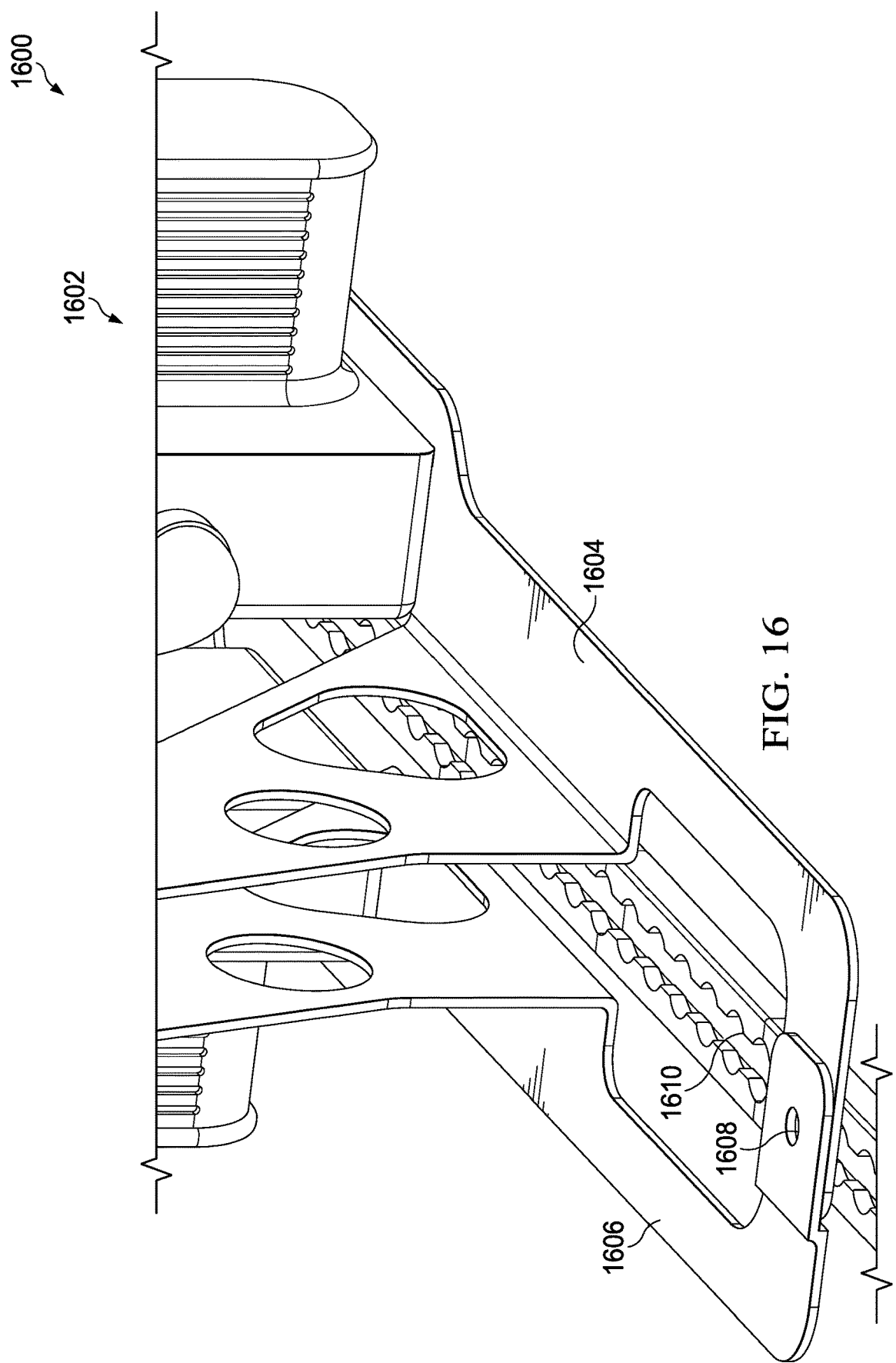
FIG. 16 is an isometric view of mounting plates of a ventilation assembly in accordance with an illustrative embodiment.

Turning now to FIG. 16, an isometric view of mounting plates of a ventilation assembly is depicted in accordance with an illustrative embodiment. Number of mounting plates 1602 can be used in aircraft 100 of FIG. 1. Number of mounting plates 1602 is a physical implementation of number of mounting plates 208 of FIG. 2 and may include mounting plate 1604 and mounting plate 1606. Mounting plate 1604 and mounting plate 1606 may each, respectively, have feature 1608, such as without limitation a through-hole configured to engage with a device (not shown) configured such that it locks mounting plate 1604 and/or mounting plate 1606 into seat track 1610. Number of mounting plates 1602 is a physical implementation of number of mounting plates 342 of FIG. 3. Seat track 1610 is a physical implementation of seat track 352 in FIG. 3. In some illustrative examples, number of mounting plates 342 is a portion of number of mounting plates 520 of FIGS. 5-13. In some illustrative examples, number of mounting plates 342 is a portion of number of mounting plates 1418 of FIG. 14.

Mounting plate 1504 of ventilation assembly 1502 comprises base 1506 and positioning feature 1510. Base 1506 is configured to connect to fan system 1508. Mounting plate 1504 is designed based on a design of fan system 1508 and a design of manifold 1512. Mounting plate 1504 is configured to provide sufficient support and strength to mount fan system 1508 and manifold 1512 to seat track 1514. At least one of a design or a material of mounting plate 1504 is selected to reduce the weight of mounting plate 1504. In some illustrative examples, cavities are present in mounting plate 1504 to reduce weight by reducing the amount of material forming mounting plate 1504.

In some illustrative examples, mounting plate 1504 is formed of a metal. In some illustrative examples, mounting plate 1504 is formed of aluminum or an aluminum alloy based on cost, weight, and strength. In some illustrative examples, mounting plate is formed of a composite material.

Figure 17:
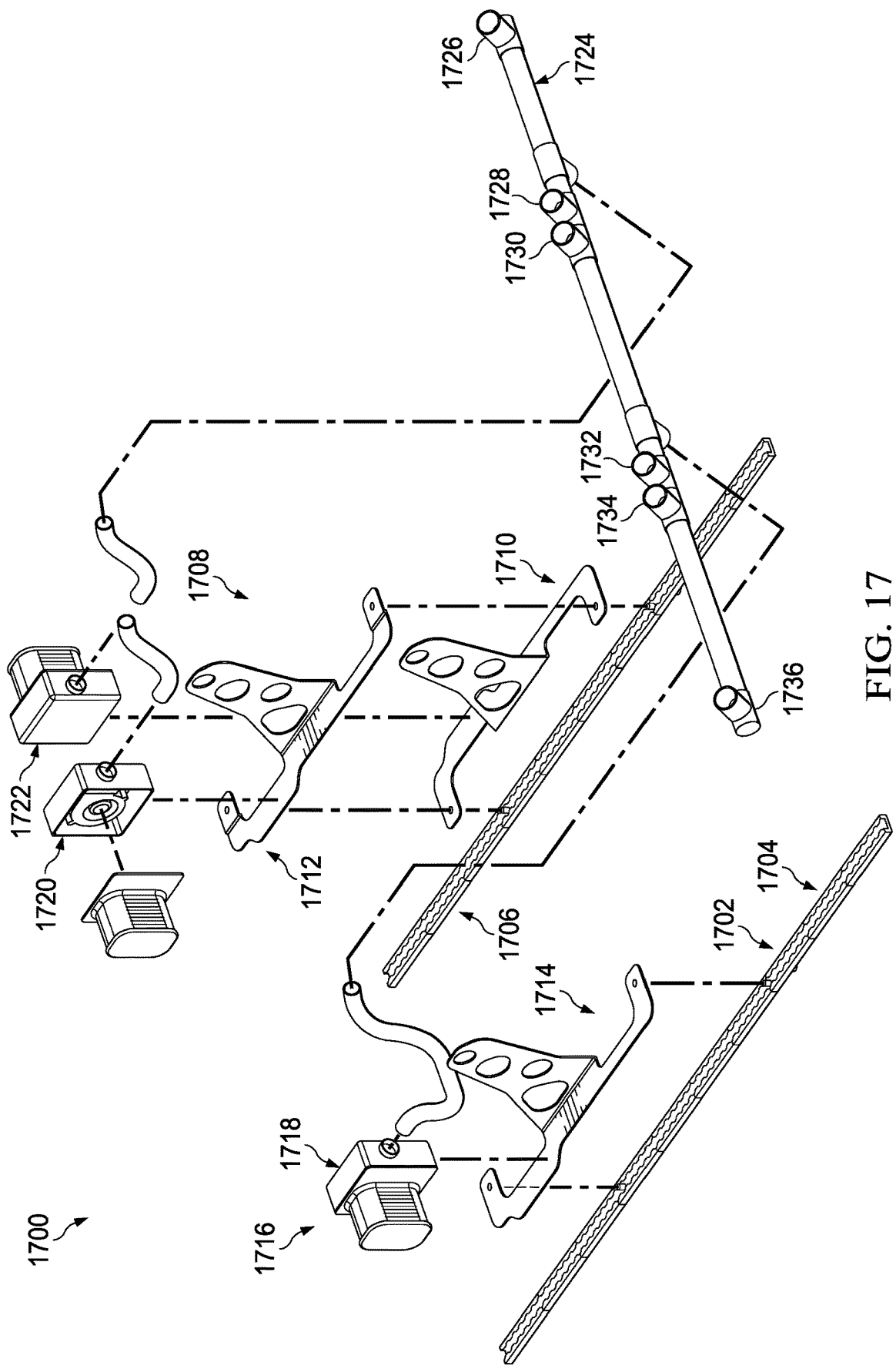
FIG. 17 is an exploded view of components of a ventilation assembly in accordance with an illustrative embodiment.

Turning now to FIG. 17, an exploded view of components of a ventilation assembly is depicted in accordance with an illustrative embodiment. View 1700 is a view of the components of a ventilation assembly that are mounted to seat tracks within a passenger cabin of an aircraft. Components 1701 in view 1700 are physical implementations of number of fan systems 202, number of mounting plates 208, and manifold 210 in FIG. 2. Components 1701 in view 1700 are physical implementations of number of fan systems 312, number of mounting plates 342, and manifold 358 of FIG. 3. Components 1701 can be used with air distribution assembly 400 of FIG. 4 to form a ventilation assembly. In some illustrative examples, view 1700 is an exploded view of components of ventilation assembly 504 of FIGS. 5-13. In some illustrative examples, view 1700 is an exploded view of ventilation assembly 1402 of FIG. 14. In some illustrative examples, fan system 1508 and mounting plate 1504 can be some of components 1701 of FIG. 17.

Components 1701 include components of a ventilation assembly that are connected either directly or indirectly to number of seat tracks 1702. Number of seat tracks 1702 include seat track 1704 and seat track 1706. Each of number of mounting plates 1708 is connected directly to one of number of seat tracks 1702. Number of mounting plates 1708 includes mounting plate 1710, mounting plate 1712, and mounting plate 1714. Each of mounting plates is connected to a respective seat track at two locations for stability. However, in other illustrative examples, a mounting plate can include more or less than two connections per mounting plate.

Each of number of mounting plates is configured to support a respective fan system and manifold 1724. Each of number of mounting plates has a base to connect to a respective fan system of number of fan systems 1716. Number of fan systems 1716 includes fan system 1718, fan system 1720, and fan system 1722.

Mounting plate 1714 is configured to connect to fan system 1718 and join fan system 1718 to seat track 1704. Mounting plate 1712 is configured to connect to fan system 1720 and join fan system 1720 to seat track 1706. Mounting plate 1710 is configured to connect to fan system 1722 and join fan system 1722 to seat track 1706.

As depicted, fan system 1720 is partially exploded to demonstrate the separate purification and fan/motor components. The fan and motor will pull the air through the purification component and send the purified air out of the fan and motor portion to ductwork.

Manifold 1724 is configured to extend through and be restrained by number of mounting plates 1708. Each of number of mounting plates 1708 is configured such that manifold 1724 can be restrained without contacting any neighboring passenger seats.

Manifold 1724 has a different design than manifold 608 of FIGS. 5-13. In some illustrative examples, manifold 1724 is an alternative to manifold 608 depicted in FIGS. 5-13. Manifold 1724 has a respective inlet for each of number of fan systems 1716. As depicted, manifold 1724 has outlet 1726, outlet 1728, outlet 1730, outlet 1732, outlet 1734, and outlet 1736. In this illustrative example, each air distribution system assembly will be connected to more than one outlet. For example, ducts (not depicted) will connect outlet 1726 and outlet 1728 to a first air distribution assembly. As another example, ducts (not depicted) will connect outlet 1730, outlet 1732 to a second air distribution assembly. As depicted, each outlet of manifold 1724 is connected to a single air distribution assembly. In FIGS. 5-13, some outlets of manifold 608 provide air to more than one air distribution assembly.

The illustration of components 1701 in FIG. 17 is not meant to imply physical or architectural limitations to the manner in which an illustrative embodiment may be implemented. Other components in addition to or in place of the ones illustrated may be used. Some components may be unnecessary. In some examples, manifold 1724 is not present.

In some non-depicted illustrative examples, there are fewer fan systems than there are mounting plates. In these illustrative examples, at least one mounting plate is not configured to support a fan system. In some illustrative examples, one of number of fan systems 1716 can have a different design than at least one other fan system in number of fan systems 1716.

Figure 18:
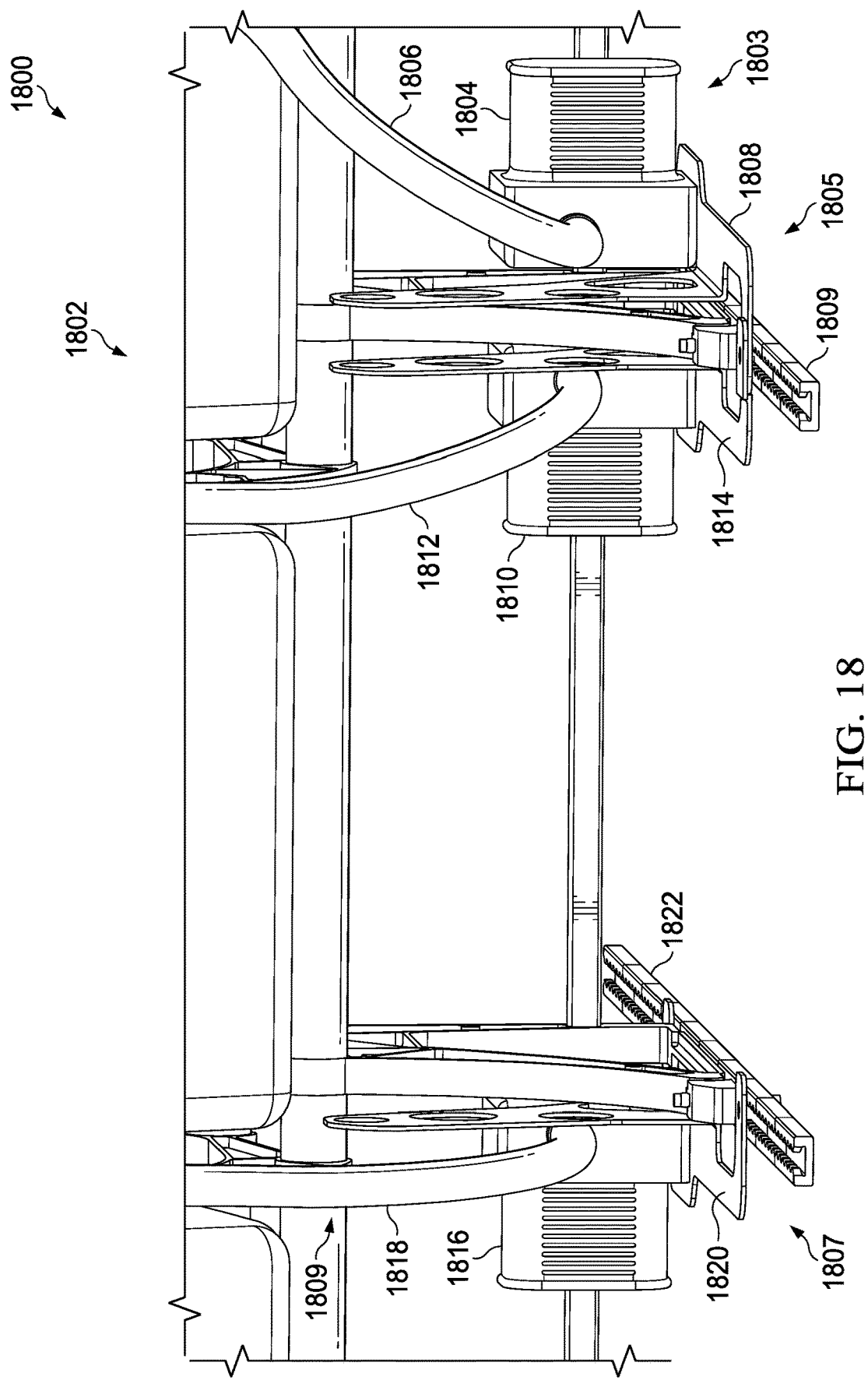
FIG. 18 is a back view of a ventilation assembly in accordance with an illustrative embodiment.

Turning now to FIG. 18, a back view of a ventilation assembly is depicted in accordance with an illustrative embodiment. Ventilation assembly 1800 can be used in aircraft 100 of FIG. 1. Ventilation assembly 1800 is a physical implementation of ventilation assembly 200 of FIG. 2. Ventilation assembly 1800 is a physical implementation of ventilation assembly 308 of FIG. 3. Components of ventilation assembly 1800 can be used with air distribution assembly 400 of FIG. 4. Ventilation assembly 1800 can be an alternate design for number of fan systems 518 and number of mounting plates 520 to be used in ventilation assembly 504 of FIGS. 5-13.

Ventilation assembly 1800 is associated with set of passenger seats 1802. Ventilation assembly 1800 comprises number of fan systems 1803 and number of mounting plates 1805. Number of mounting plates 1805 is connected to number of seat tracks 1807. Ductwork 1809 connects number of fan systems 1803 to a number of air distribution assemblies. In some illustrative examples, ductwork 1809 is configured to not undesirably interfere with egress from any of the passenger seats in set of passenger seats 1802.

In this illustrative example, number of fan systems 1803 comprises three fan systems. Purified air is sent from fan system 1804 through duct 1806 to an air distribution assembly (not depicted). Fan system 1804 is connected to mounting plate 1808. Mounting plate 1808 connects fan system 1804 to seat track 1811.

Purified air is sent from fan system 1810 through duct 1812 to an air distribution assembly (not depicted). Fan system 1810 is connected to mounting plate 1814. Mounting plate 1814 connects fan system 1810 to seat track 1811. Mounting plate 1814 overlaps mounting plate 1808.

Purified air is sent from fan system 1816 through duct 1818 to an air distribution assembly (not depicted). Fan system 1816 is connected to mounting plate 1820. Mounting plate 1820 connects fan system 1810 to seat track 1822.

In this illustrative example, purified air from a fan system is directed to a respective air distribution assembly. In this illustrative example, a manifold is not present in ventilation assembly 1900.

Figure 19:
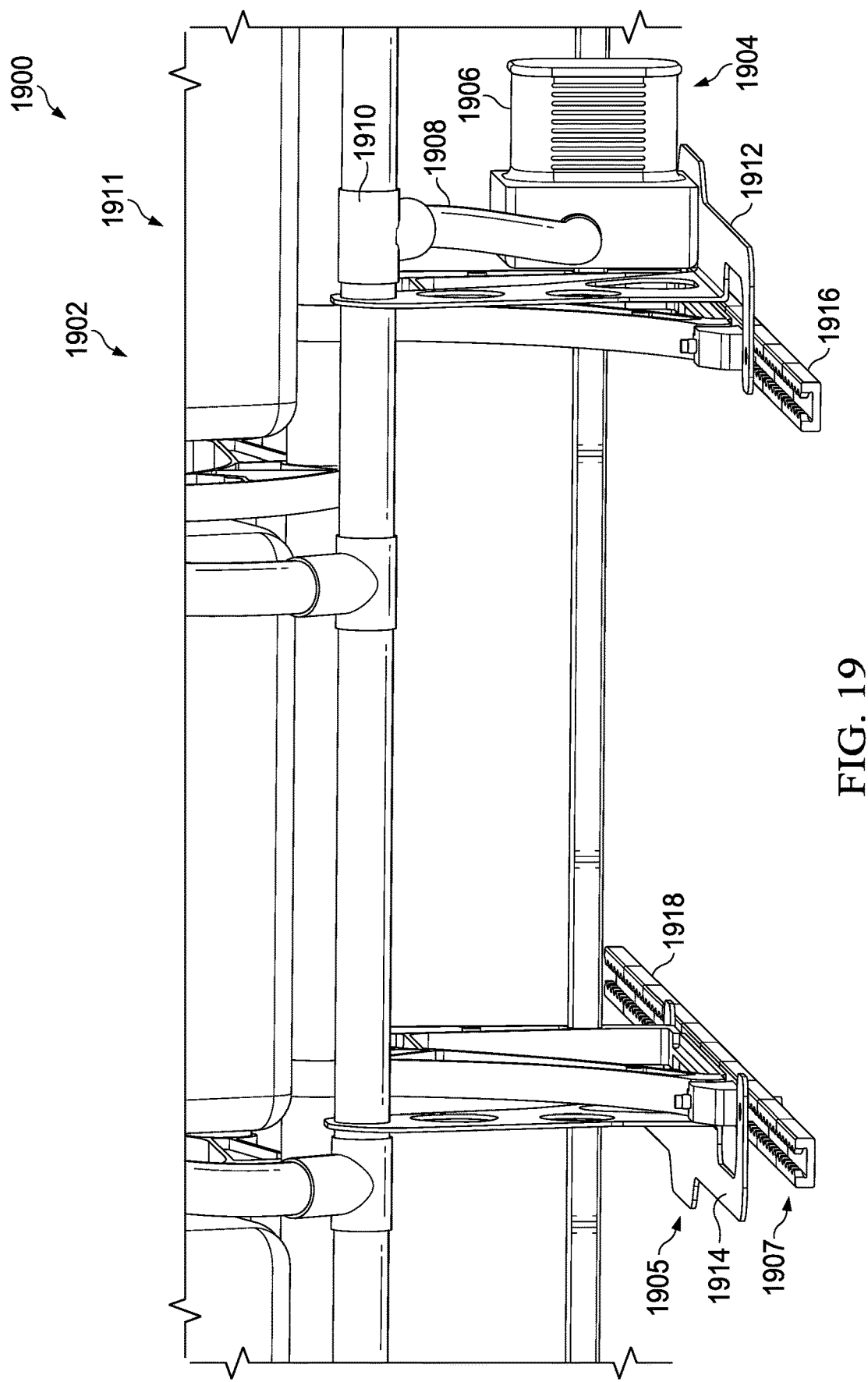
FIG. 19 is a back view of a ventilation assembly in accordance with an illustrative embodiment.

Turning now to FIG. 19, a back view of a ventilation assembly is depicted in accordance with an illustrative embodiment. Ventilation assembly 1900 can be used in aircraft 100 of FIG. 1. Ventilation assembly 1900 is a physical implementation of ventilation assembly 200 of FIG. 2. Ventilation assembly 1900 is a physical implementation of ventilation assembly 308 of FIG. 3. Components of ventilation assembly 1900 can be used with air distribution assembly 400 of FIG. 4. Ventilation assembly 1900 can be an alternate design for number of fan systems 518 and number of mounting plates 520 to be used in ventilation assembly 504 of FIGS. 5-13.

Ventilation assembly 1900 is associated with set of passenger seats 1902. Ventilation assembly 1900 comprises number of fan systems 1904 and number of mounting plates 1905. Number of mounting plates 1905 is configured to connected to number of seat tracks 1907.

Number of fan systems 1904 includes fan system 1906. In this illustrative example, fan system 1906 is the only fan system in ventilation assembly 1900. Fan system 1906 is selected based on weight, power usage, pressure and flow rate, and noise. Ductwork 1908 connects fan system 1906 to manifold 1910. Manifold 1910 is configured to distribute purified air from fan system 1906 to multiple air distribution assemblies.

In this illustrative example, fan system 1906 is restrained in passenger cabin 1902 by mounting plate 1912. Mounting plate 1912 connects fan system 1906 to seat track 1916. Mounting plate 1912 also restrains manifold 1910 within passenger cabin 1902. Mounting plate 1912 connects manifold 1910 to seat track 1916.

Mounting plate 1914 is connected to seat track 1918. No fan system is connected to mounting plate 1914. Mounting plate 1914 restrains manifold 1910 within passenger cabin 1902. Mounting plate 1914 connects manifold 1910 to seat track 1918.

Figure 20:
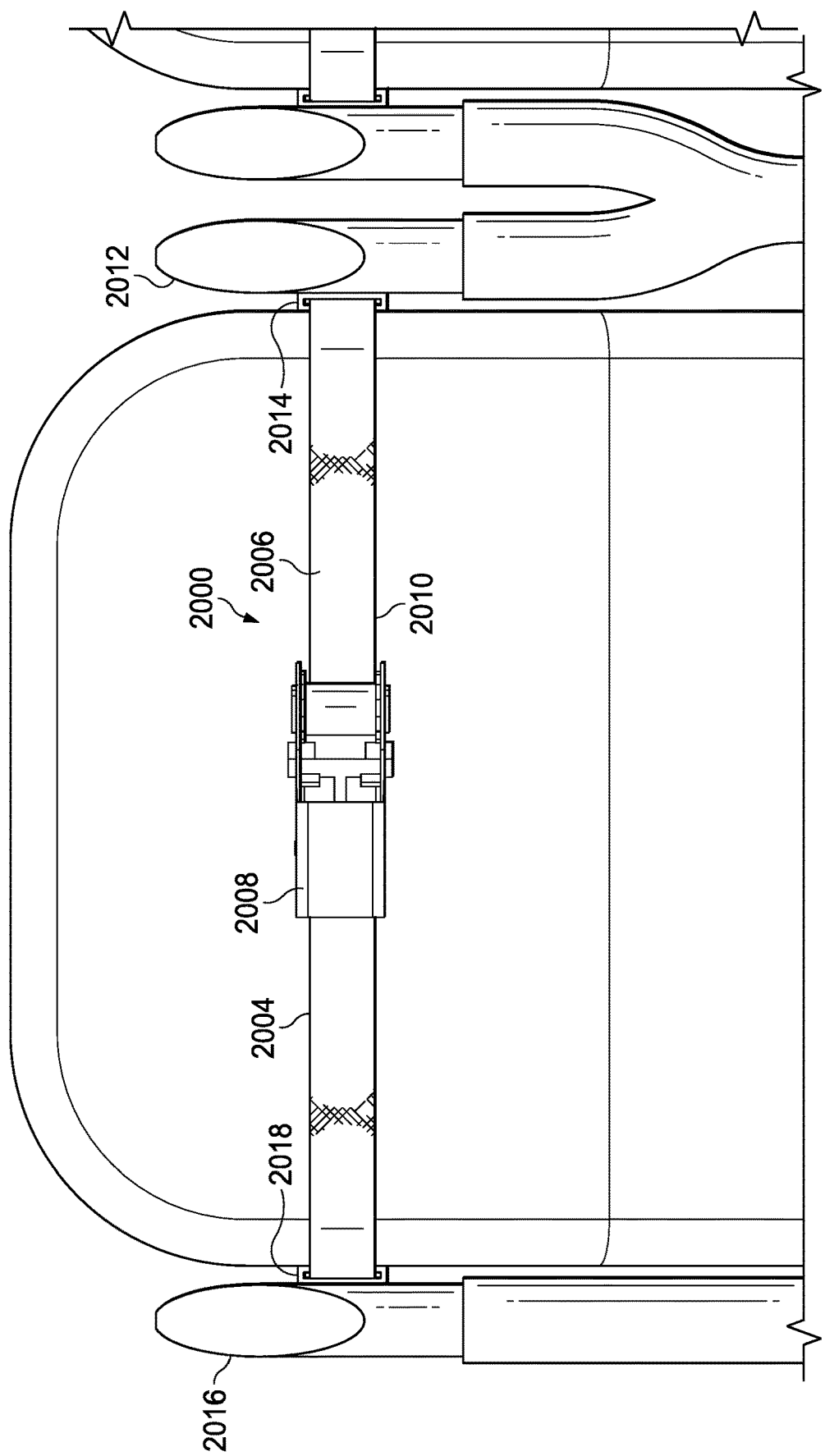
FIG. 20 is an isometric view of an air distribution assembly in accordance with an illustrative embodiment.

Turning now to FIG. 20, an isometric view of an air distribution assembly is depicted in accordance with an illustrative embodiment. Air distribution assembly 2000 can be used in aircraft 100 of FIG. 1. Air distribution assembly 2000 is a physical implementation of one of number of air distribution assemblies 204 of FIG. 2. Air distribution assembly 2000 is a physical implementation of one of number of air distribution assemblies 314 of FIG. 3. Air distribution assembly 2000 is a physical implementation of air distribution assembly 400 of FIG. 4. Air distribution assembly 2000 can be an alternate design for an air distribution assembly to be used in ventilation assembly 504 of FIGS. 5-13. Air distribution assembly 2000 can be used in ventilation assembly 1402 of FIG. 14. Air distribution assembly 2000 can be used in ventilation assembly 1502 of FIG. 15. Air distribution assembly 2000 can be used in a ventilation assembly along with number of mounting plates 1602 of FIG. 16. Air distribution assembly 2000 can be used with components 1701 of FIG. 17 in a ventilation assembly. Air distribution assembly 2000 can be used in ventilation assembly 1800 of FIG. 18. Air distribution assembly 2000 can be used in ventilation assembly 1900 of FIG. 19.

Air distribution assembly 2000 comprises pair of air distribution vents 2002 and seat attachment device 2004. Seat attachment device 2004 is configured to removably couple pair of air distribution vents 2002 to a seatback such that each air distribution vent is situated on opposite sides of the seatback for providing purified air to a seated passenger. In this illustrative example, seat attachment device 2004 comprises ratchet belt 2006. Ratchet belt 2006 includes ratchet 2008 and belt 2010. Ratchet 2008 allows for seat attachment device 2004 to be adjustable. Ratchet 2008 can be used to adjust a length of belt 2010 used to encircle the seatback of the passenger seat.

Belt 2010 is formed of any desirable material. In some illustrative examples, material of belt 2010 is selected based on weight. In some illustrative examples, belt 2010 comprises elastic material. In some illustrative examples, material for belt 2010 is selected to be a non-stretch material.

In this illustrative example, positions of pair of air distribution vents 2002 are adjustable along belt 2010. Each of pair of air distribution vents 2002 is connected to belt 2010 by a respective slider. Left vent 2012 is connected to belt 2010 by slider 2014. Right vent 2016 is connected to belt 2010 by slider 2018.

Although ductwork is not depicted in FIG. 20, any desirable design of ductwork can be used to provide purified air to pair of air distribution vents 2002. In some illustrative examples, flexible ductwork is used to provide purified air to pair of air distribution vents 2002.

Figure 21:
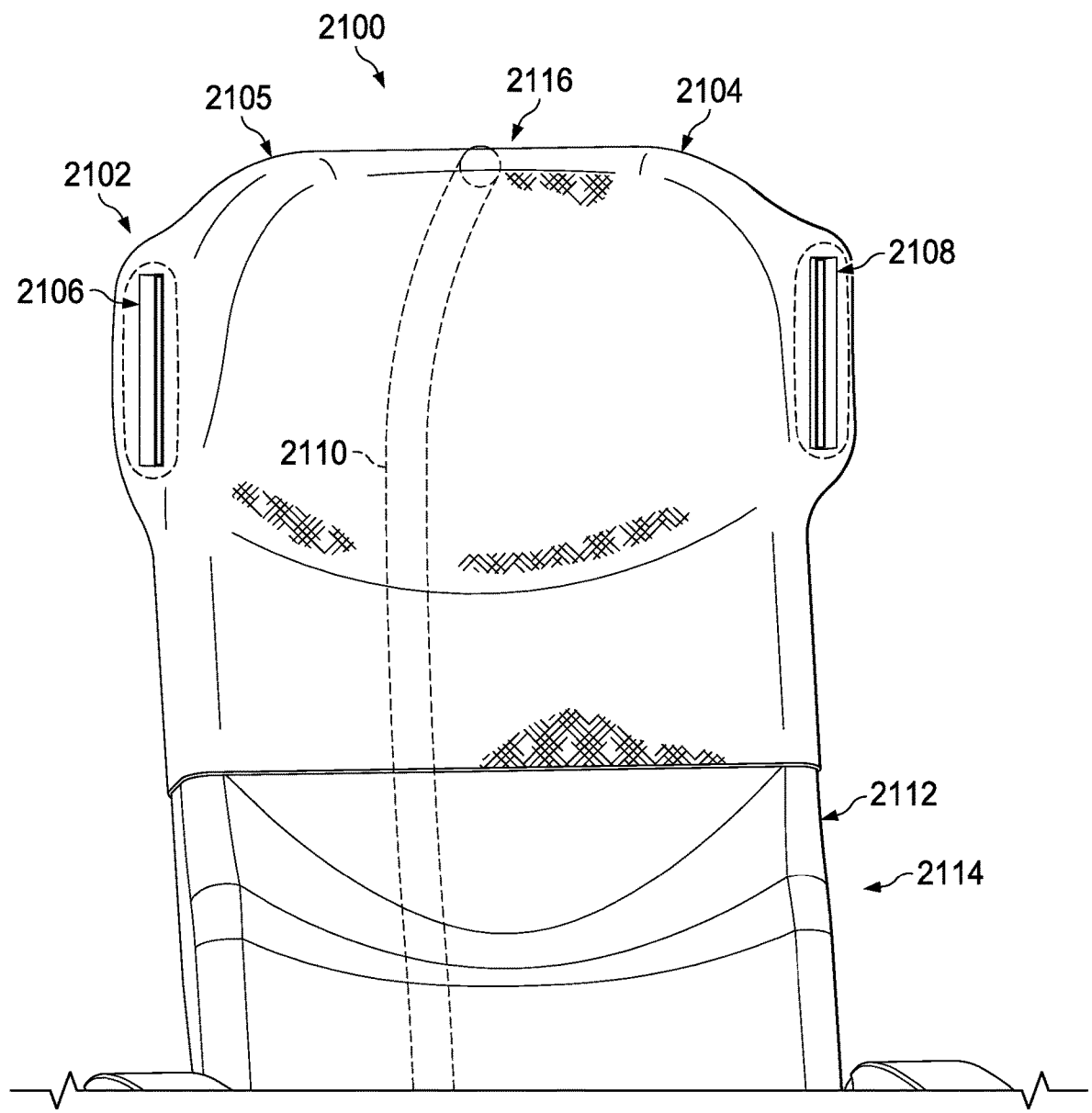
FIG. 21 is an isometric view of an air distribution assembly in accordance with an illustrative embodiment.

Turning now to FIG. 21, an isometric view of an air distribution assembly is depicted in accordance with an illustrative embodiment. Air distribution assembly 2100 can be used in aircraft 100 of FIG. 1. Air distribution assembly 2100 is a physical implementation of one of number of air distribution assemblies 204 of FIG. 2. Air distribution assembly 2100 is a physical implementation of one of number of air distribution assemblies 314 of FIG. 3. Air distribution assembly 2100 is a physical implementation of air distribution assembly 400 of FIG. 4. Air distribution assembly 2100 can be an alternate design for an air distribution assembly to be used in ventilation assembly 504 of FIGS. 5-13. Air distribution assembly 2100 can be used in ventilation assembly 1402 of FIG. 14. Air distribution assembly 2100 can be used in ventilation assembly 1502 of FIG. 15. Air distribution assembly 2100 can be used in a ventilation assembly along with number of mounting plates 1602 of FIG. 16. Air distribution assembly 2100 can be used with components 1701 of FIG. 17 to form a ventilation assembly. Air distribution assembly 2100 can be used in ventilation assembly 1800 of FIG. 18. Air distribution assembly 2100 can be used in ventilation assembly 1900 of FIG. 19.

Air distribution assembly 2100 comprises pair of air distribution vents 2102 and seat attachment device 2104. Seat attachment device 2104 is configured to removably couple pair of air distribution vents 2102 to a seatback such that each air distribution vent is situated on opposite sides of the seatback for providing purified air to a seated passenger. In this illustrative example, seat attachment device 2104 comprises slipcover 2105. In some illustrative examples, slipcover 2105 comprises an elastic material. When present, elastic allows for seat attachment device 2104 to be adjustable. When slipcover 2105 comprises an elastic material, slipcover 2105 can be expanded to encircle seatback 2112 of a passenger seat 2114.

In this illustrative example, positions of pair of air distribution vents 2102 are set within slipcover 2105. Each of pair of air distribution vents 2002 is directly connected to slipcover 2105. Left vent 2106 and right vent 2108 receive purified air from ductwork 2110. In this illustrative example, ductwork 2110 is flexible.

Slipcover 2105 covers headrest 2116 of passenger seat 2114. Slipcover 2105 is designed to position left vent 2106 and right vent 2108 at a set height of seatback 2112 of passenger seat 2114. By covering the top of headrest 2116 seat attachment device 2104 indexes the height of air distribution device 2100 to a set height on passenger seat 2114.

Figure 22:
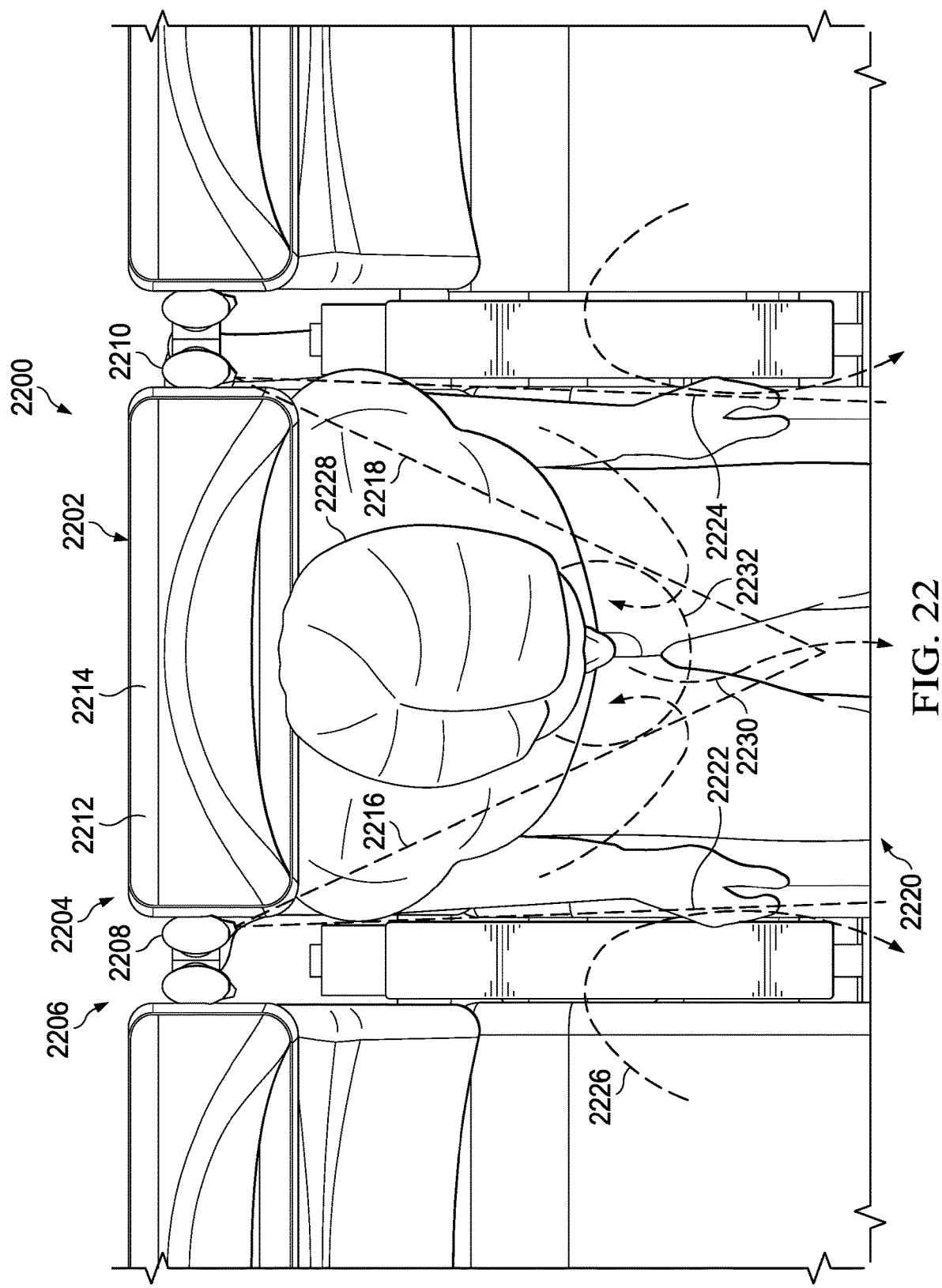
FIG. 22 is a top view of an air distribution assembly attached to a passenger seat in accordance with an illustrative embodiment.

Turning now to FIG. 22, a top view of an air distribution assembly attached to a passenger seat is depicted in accordance with an illustrative embodiment. View 2200 can be a view within aircraft 100 of FIG. 1. Ventilation assembly 2202 is a physical implementation of ventilation assembly 200 of FIG. 2. Ventilation assembly 2202 is a physical implementation of ventilation assembly 308 of FIG. 3. Components of ventilation assembly 2202 are physical implementations of air distribution assembly 400 of FIG. 4. In some illustrative examples, ventilation assembly 2202 can be the same as ventilation assembly 504 of FIGS. 5-13. Ventilation assembly 2202 can include any of the number of fan system designs and any of the mounting plate designs depicted in FIGS. 14-19. Any of air distribution assembly 2000 of FIG. 20 air distribution assembly 2100 of FIG. 21 can be utilized in ventilation assembly 2202 of FIG. 22.

FIG. 22 depicts an overhead view of a breathing space that may be filled and isolated by a first airflow and a second airflow, in accordance with an illustrative embodiment. More specifically, FIG. 22 depicts ventilation assembly 2202 having air distribution assembly 2204. Air distribution assembly 2204 comprises pair of air distribution vents 2206. Pair of air distribution vents 2206 include left vent 2208 and right vent 2210 on opposite sides of headrest 2212 of passenger seat 2214.

Pair of air distribution vents 2206 are configured to and positioned to create a triangular pattern of clean airflow. Each of air distribution vents 2206 is configured such that the purified air diverges into the triangular airflow. Left vent 2208 is configured to generate airflow 2216. Right vent 2210 is configured to generate airflow 2218.

Airflow 2216 may combine with airflow 2218 to form breathing space 2220, in accordance with an illustrative embodiment. An outside edge of airflow 2216 can function as barrier 2222. An outside edge of airflow 2218 may function as barrier 2224.

The illustrative examples create a larger area flow that helps to divert ambient air 2226 away from passenger 2228. Left vent 2208 and right vent 2210 produce airflow 2216 and airflow 2218 that displace ambient air 2226 in breathing space 2220 with purified air supplied to air distribution assembly 2204. Ambient air 2226 is air outside of breathing space 2220. Ambient air 2226 may be a cabin air that occupies the same volume of space that becomes breathing space 2220 before left vent 2208 and right vent 2210 begin to operate and create breathing space 2220 by displacing the cabin air in that space with purified air. Thus, airflow 2216 and airflow 2218 can suffuse or substantially fill breathing space 2220 with purified air.

The illustrative examples can eject exhaled air 2230 of passenger 2228 forward. But at the same time the triangular flow created by air distribution assembly 2204 tends to overwhelm any ambient air entering from behind passenger seat 2214 and leaves passenger 2228 with a pocket of clean filtered air in inhalation sphere 2232. Inhalation sphere 2232 may be a volume of air that may be inhaled by passenger 2228 through their mouth and/or nose.

Breathing space 2220 may occupy a volume of air that may provide a source of air that may suffuse or fill and envelope inhalation sphere 2232 for passenger 2228. To create breathing space 2220 of purified air that will envelope a full range of sizes and locations for inhalation sphere 2232 for different passenger sizes, the breathing space 2220 may be either adjustable for each individual passenger, envelope the entire dimensions of all the possible inhalation spheres, or some combination thereof. If the breathing space 2220 is adjustable, envelopes the dimensions for all possible inhalation spheres, or some combination thereof the inhalation sphere of a particular passenger has purified air delivered to suffuse or to fully occupy the dimensions of the particular passenger's inhalation sphere 2232. In some illustrative examples, breathing space 2220 is adjustable by adjusting a position of air distribution assembly 2204 along a height of the seatback of passenger seat 2214.

Any contaminants present in the ambient air that enters breathing space 2220 are dissipated and made significantly rarer by movement and volume of airflow 2216 and airflow 2218. Broader air patterns and overwhelming the area around a passenger's face with purified air is effective at providing protection from potential contamination in the ambient air that has yet to be filtered by personal or aircraft wide environmental systems. In some illustrative examples, airflow 2216 and airflow 2218 provide obstacles equivalent to a face mask worn by a passenger.

Airflow 2216 and airflow 2218 are directed such that the edges of airflow 2216 and airflow 2218 barely pass by the front of the cheeks and ears of passenger 2228. Passengers have a high sensitivity to air motion and temperature. Strong flow directly onto passenger 2228 can cause passenger 2228 to feel chilled or feel a draft. Airflow 2216 and airflow 2218 provides substantial amounts of purified air to passenger 2228 and moves the air to divert ambient air 2226 away from passenger 2228. Airflow 2216 and airflow 2218 provides benefit without causing discomfort to the passenger.

Breathing space may be bounded by barrier 2222 and by barrier 2224. Each barrier can at least partially impede transgression of ambient air 2226 from crossing through the respective barrier and entering into breathing space 2220. Each barrier, barrier 2222 and barrier 2224 may retain purified air from crossing through the respective barrier and exiting breathing space 2220.

Purified air can be delivered from a purified air source. The purified air source may provide air that is substantially free of virus and/or bacterial contaminants or other allergens and/or irritants that may come from any origin, such as without limitation, the exhalation of any other person, or any item, clothing, and/or skin of anyone near and/or in passenger seat or the passenger cabin, in accordance with an illustrative embodiment.

Left vent 2208 and right vent 2210 may be of similar design and/or construction, of inverse design and/or construction relative to each other, of unique design and/or construction relative to each other, or of any combination thereof. Each vent may include, an outlet, a nozzle, an airflow guide system, a baffle, or any structure such that airflow exiting each vent may exit with a desired shape, pressure and flow rate, and velocity distribution to provide breathing space 2220.

Airflow 2216 and airflow 2218 substantially suffuse or fills inhalation sphere 1308 within breathing space 2220 with purified air. In some illustrative examples, ambient air 2226 outside of breathing space 2220 may not be entrained into airflow 2216 or airflow 2218 or be able to cross through airflow 2216 or airflow 2218 into breathing space 2220.

Figure 23:
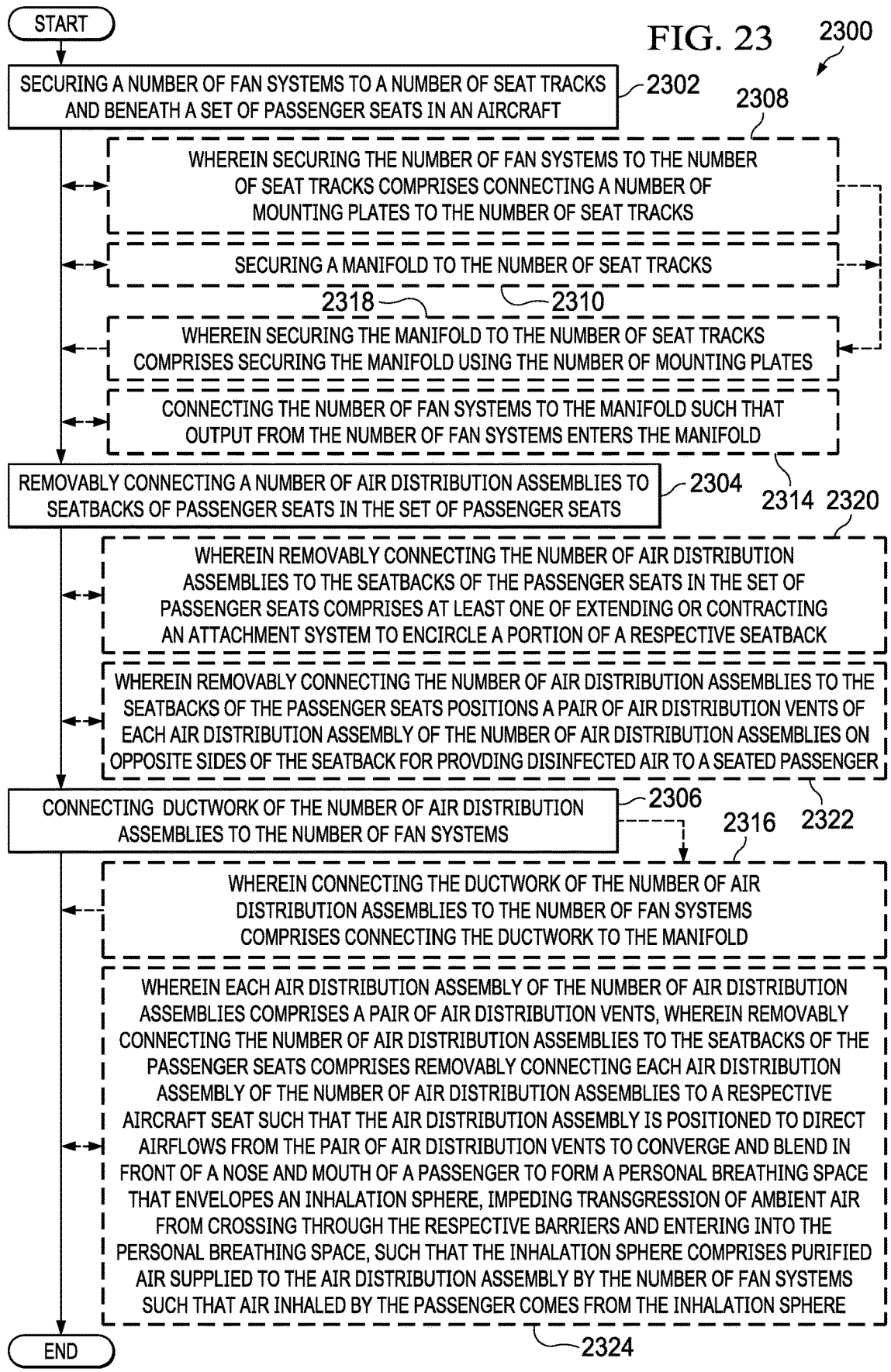
FIG. 23 is an illustration of a flowchart of a method of installing a ventilation assembly in accordance with an illustrative embodiment.

Turning now to FIG. 23, an illustration of a flowchart of a method of installing a ventilation assembly is depicted in accordance with an illustrative embodiment. Method 2300 can be used to install a ventilation assembly in aircraft 100 of FIG. 1. Method 2300 can be used to install ventilation assembly 200 of FIG. 2. Method 2300 can be used to install a ventilation assembly within aircraft 300 of FIG. 3. Method 2300 can be used to install a ventilation assembly including air distribution assembly 400 of FIG. 4. Method 2300 can be used to install ventilation assembly 504 of FIGS. 5-13. Method 2300 can be used to install ventilation assembly 1402 in FIG. 14. Method 2300 can be used to install ventilation assembly 1502 in FIG. 15. Method 2300 can be used to install a ventilation assembly including mounting plate 1604 and mounting plate 1606 in FIG. 16. Method 2300 can be used to install components 1701 of FIG. 17. Method 2300 can be used to install ventilation assembly 1800 in FIG. 18. Method 2300 can be used to install ventilation assembly 1900 in FIG. 19. Method 2300 can be used to install a ventilation assembly with air distribution assembly 2000 in FIG. 20. Method 2300 can be used to install a ventilation assembly with air distribution assembly 2100 in FIG. 21. Method 2300 can be used to install ventilation assembly 2202 in FIG. 22.

Method 2300 secures a number of fan systems to a number of seat tracks and beneath a set of passenger seats in an aircraft (operation 2302). The number of fan systems comprises any quantity of fan systems. By the number of fan systems being mounted to the seat tracks, the weight of the load of the number of fan systems is not carried through the passenger seats.

Method 2300 removably connects a number of air distribution assemblies to seatbacks of passenger seats in the set of passenger seats (operation 2304). The number of air distribution assemblies is removably connected by a seat attachment device. Method 2300 connects ductwork of the number of air distribution assemblies to the number of fan systems (operation 2306). Afterwards, method 2300 terminates.

By connecting the ductwork to the number of fan systems, the purified air from the number of fan systems will be delivered to the number of air distribution assemblies. The ductwork can be either directly or indirectly connected to the number of fan systems.

A first component is considered to be indirectly connected to a second component when one or more additional components are present between the two components. When the first component is directly connected to the second component, no additional components are present between the two components.

In some illustrative examples, securing the number of fan systems to the number of seat tracks comprises connecting a number of mounting plates to the number of seat tracks (operation 2308). In some illustrative examples, method 2300 secures a manifold to the number of seat tracks (operation 2310). In some illustrative examples, method 2300 connects the number of fan systems to the manifold such that output from the number of fan systems enters the manifold (operation 2314). In some illustrative examples, connecting the ductwork of the number of air distribution assemblies to the number of fan systems comprises connecting the ductwork to the manifold (operation 2316).

In some illustrative examples, securing the number of fan systems to the number of seat tracks comprises connecting a number of mounting plates to the number of seat tracks (operation 2308). In some illustrative examples, securing the manifold to the number of seat tracks comprises securing the manifold using the number of mounting plates (operation 2318).

In some illustrative examples, removably connecting the number of air distribution assemblies to the seatbacks of the passenger seats in the set of passenger seats comprises at least one of extending or contracting an attachment system to encircle a portion of a respective seatback (operation 2320). In some illustrative examples, removably connecting the number of air distribution assemblies to the seatbacks of the passenger seats positions a pair of air distribution vents of each air distribution assembly of the number of air distribution assemblies on opposite sides of the seatback for providing purified air to a seated passenger (operation 2322).

In some illustrative examples, each air distribution assembly of the number of air distribution assemblies comprises a pair of air distribution vents, wherein removably connecting the number of air distribution assemblies to the seatbacks of the passenger seats comprises removably connecting each air distribution assembly of the number of air distribution assemblies to a respective passenger seat such that the air distribution assembly is positioned to direct airflows from the pair of air distribution vents to converge and blend in front of a nose and mouth of a passenger to form a personal breathing space that envelopes an inhalation sphere, impeding transgression of ambient air from crossing through the respective barriers and entering into the personal breathing space, such that the inhalation sphere comprises purified air supplied to the air distribution assembly by the number of fan systems such that air inhaled by the passenger comes from the inhalation sphere (operation 2324). Although the airflows will not prevent all ambient air from entering the personal breathing space, the movement of the airflows will divert ambient air away from the personal breathing space. Additionally, although the airflows will not prevent all ambient air from entering the personal breathing space, the moving airflow will significantly dissipate any ambient air that is able to enter the personal breathing space. The airflow will effectively overwhelm the space around a passenger's face with purified air.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram. Some blocks may be optional. For example, any of operation 2306 through operation 2324 may be optional.

Figure 24:
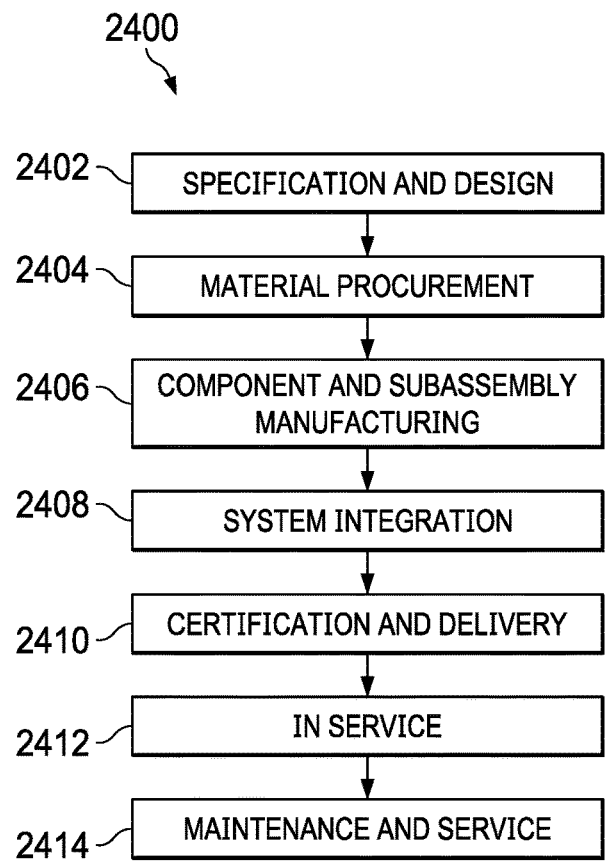
FIG. 24 is an illustration of an aircraft manufacturing and service method in a form of a block diagram in accordance with an illustrative embodiment.
Figure 25:
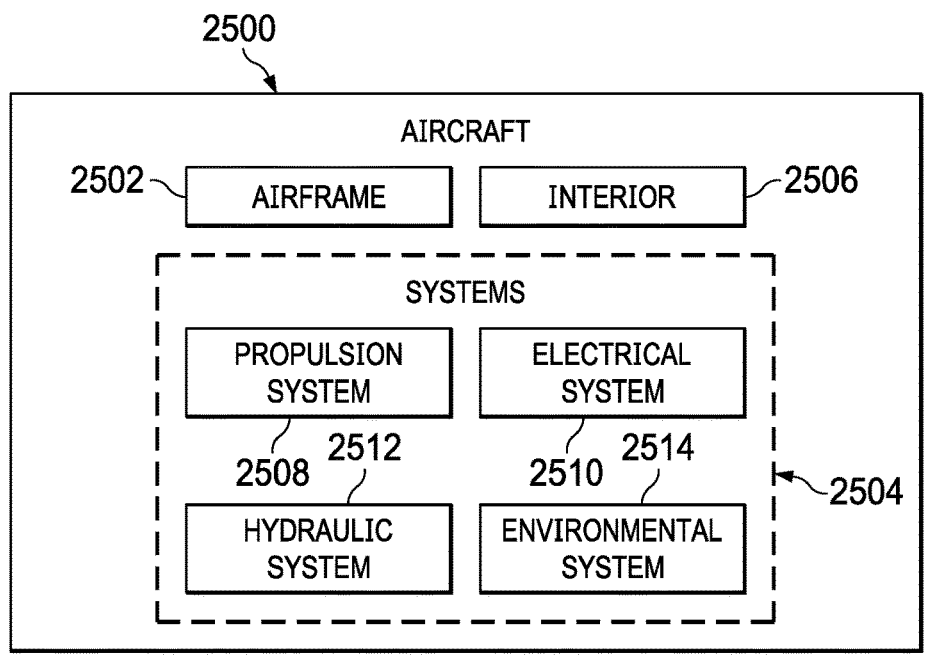
FIG. 25 is an illustration of an aircraft in a form of a block diagram in which an illustrative embodiment may be implemented.

Illustrative embodiments of the present disclosure may be described in the context of aircraft manufacturing and service method 2400 as shown in FIG. 24 and aircraft 2500 as shown in FIG. 25. Turning first to FIG. 24, an illustration of an aircraft manufacturing and service method is depicted in accordance with an illustrative embodiment. During pre-production, aircraft manufacturing and service method 2400 may include specification and design 2402 of aircraft 2500 in FIG. 25 and material procurement 2404.

During production, component and subassembly manufacturing 2406 and system integration 2408 of aircraft 2500 takes place. Thereafter, aircraft 2500 may go through certification and delivery 2410 in order to be placed in service 2412. While in service 2412 by a customer, aircraft 2500 is scheduled for routine maintenance and service 2414, which may include modification, reconfiguration, refurbishment, or other maintenance and service.

Each of the processes of aircraft manufacturing and service method 2400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 25, an illustration of an aircraft is depicted in which an illustrative embodiment may be implemented. In this example, aircraft 2500 is produced by aircraft manufacturing and service method 2400 of FIG. 24 and may include airframe 2502 with plurality of systems 2504 and interior 2506. Examples of systems 2504 include one or more of propulsion system 2508, electrical system 2510, hydraulic system 2512, and environmental system 2514. Any number of other systems may be included.

Apparatuses and methods embodied herein may be employed during at least one of the stages of aircraft manufacturing and service method 2400. One or more illustrative embodiments may be manufactured or used during at least one of component and subassembly manufacturing 2406, system integration 2408, in service 2412, or maintenance and service 2414 of FIG. 24.

Ventilation assemblies, such as ventilation assembly 200 can be used to provide purified air during in service 2412. A ventilation assembly, such as ventilation assembly 200, can be installed during maintenance and service 2414. Method 2300 can be performed during component and subassembly manufacturing 2406. Method 2300 can be performed during maintenance and service 2414.

The illustrative examples provide retrofit ventilation assemblies. The illustrative examples may provide lighter ventilation assemblies than built-in integrated ventilation seats. The illustrative examples can be quickly added to existing passenger seats. The illustrative examples provide a modular set of equipment that can be used on variety of different designs of passenger seats. The illustrative examples provide novel ways to design a ventilation assembly such that it can be pre-assembled and easily slipped onto existing seating.

The illustrative examples are split up into two major sets of components, components connected to a passenger seat and components mounted to seat tracks. The components connected to the passenger seat are beneath a threshold weight restriction of what can be added onto any passenger seat without causing major redesign or recertification.

An air distribution assembly is a portion of the ventilation assembly configured to connect to a passenger seat. The air distribution assembly has a seat attachment device to connect the air distribution assembly to the passenger seat. The seat attachment device takes any desirable form that adjusts to encircle a portion of the passenger seat. In some illustrative examples, a "sock" slipcover design is present that includes the head rest clean air venting. In some illustrative examples, the slipcover includes integrated ducting and/or fabric ducting and can easily be slipped over existing seats and held in place with elastic, straps or Velcro.

The ventilation assembly also includes mounting plates that bolt down to the existing seat tracks fore and aft of the existing seat attach points. Heavier items such as fans, filters and manifolds are attached to the mounting plates. Loading is therefore carried through to the seat tracks, thereby eliminating it as a concern for excess loading on existing seat designs. By components being connected to the seat tracks, the illustrative examples present a retrofit that would not require a complete recertification of existing passenger seats. The illustrative examples include fans, filters and sound muffling mounted at floor level. The air moving equipment would be powered by passenger seat power, which is an option purchased by many Boeing customers.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A ventilation assembly that comprises:
    a plate configured to removably connect directly to a seat track and directly to a fan system configured to also connect to a power outlet in a passenger seat, wherein the plate comprises a base and a positioning feature that extends orthogonally from the base; and
    an air distribution assembly configured to be removably installed on a seatback of the passenger seat, wherein the air distribution assembly comprises:
    a pair of air distribution vents;
    ductwork configured to receive air from the fan system and direct air to the pair of air distribution vents; and
    a seat attachment device configured to removably couple the pair of air distribution vents to the seatback such that each air distribution vent is situated on opposite sides of the seatback.

2. The ventilation assembly of claim 1, further comprising a second fan system connected to a second plate connected to the seat track.

3. The ventilation assembly of claim 1 further comprising:
    a manifold configured to connect the fan system to the air distribution assembly, wherein the manifold is configured to receive output of the fan system, and wherein the manifold is configured to supply air to the air distribution assembly.

4. The ventilation assembly of claim 3 further comprising:
    a second plate configured to attach to the seat track, the second plate comprises:
        a base configured to join to a second fan system; and
        the positioning feature is configured to restrain the manifold.

5. The ventilation assembly of claim 1, wherein the plate comprises a base configured to join to the fan system.

6. The ventilation assembly of claim 1, wherein the seat attachment device is configured to encircle a portion of the seatback to removably couple the pair of air distribution vents to the seatback such that each air distribution vent is situated on opposite sides of the seatback for providing purified air to a seated passenger.

7. The ventilation assembly of claim 1, wherein the seat attachment device comprises one of elastic or a ratchet.

8. The ventilation assembly of claim 1, wherein each fan system of is further configured to comprise a female power outlet.

9. The ventilation assembly of claim 1, wherein the air distribution assembly is connected to the plate such that a weight of the air distribution assembly is supported by the plate.

10. The ventilation assembly of claim 1, wherein the fan system comprises at least one of: UV sanitizing equipment, an electric filter, or a mechanical air filter.

11. The ventilation assembly of claim 1, wherein the air distribution assembly is configured, to direct purified airflows from the pair of air distribution vents to converge and blend in front of a nose and mouth of a passenger and form a personal breathing space that envelopes an inhalation sphere suffused with a purified air comprises purified air.

12. A ventilation assembly that comprises:
    a plate configured to removably connect directly to a seat track of an aircraft and directly to a fan system configured to also connect to a power outlet in a passenger seat of an aircraft, wherein the plate comprises a base and a positioning feature that extends orthogonally from the base;
    a manifold configured to connect to the fan system and distribute air from the fan system to a number of air distribution assemblies, wherein each air distribution assembly of the number of air distribution assemblies is configured to be removably installed on a seatback of a passenger seat and comprises:
    a pair of air distribution vents;
    ductwork configured to direct air from the manifold to the air distribution vents; and
    a seat attachment device configured to removably couple the pair of air distribution vents to the seatback such that each air distribution vent is situated on opposite sides of the seatback and configured to provide purified air to an inhalation sphere at the passenger seat.

13. The ventilation assembly of claim 12, wherein each fan system is further configured to comprise a female power outlet.

14. The ventilation assembly of claim 12, wherein each air distribution assembly of the number of air distribution assemblies is connected to the plate such that a weight of the air distribution assembly is supported by the plate.

15. The ventilation assembly of claim 12, wherein the fan system comprises at least one of: UV sanitizing equipment, an electric filter, or a mechanical air filter.

16. The ventilation assembly of claim 12, wherein the seat attachment device comprises one of elastic or a ratchet.

17. The ventilation assembly of claim 12, wherein the manifold comprises a number of flow restrictors configured to substantially equalize pressure and flow rate of an air supply from the manifold to each air distribution assembly.

18. A ventilation assembly that comprises:
    a plate configured to removably connect directly to a track and directly to a fan system configured to also connect to a power outlet in a passenger seat, wherein the plate comprises a base and a positioning feature that extends orthogonally from the base
    a manifold configured to distribute air from the fan system to a number of air distribution assemblies, wherein each air distribution assembly of the number of air distribution assemblies is configured to be removably installed on a seatback of the passenger seat.

19. The ventilation assembly of claim 18, wherein the manifold comprises a number of flow restrictors configured to substantially equalize pressure and flow rate of the air supplied by the manifold to each air distribution assembly.

20. The ventilation assembly of claim 18, wherein each air distribution assembly of the number of air distribution assemblies comprises:
    a pair of air distribution vents;
    ductwork configured to receive air from at least one fan system of the number of fan systems and direct air to the pair of air distribution vents; and
    a seat attachment device configured to removably couple the pair of air distribution vents to the seatback such that each air distribution vent is situated on opposite sides of the seatback and configured to provide purified air to an inhalation sphere at the passenger seat.

21. The ventilation assembly of claim 20, wherein the seat attachment device is configured to encircle a portion of the seatback to removably couple the pair of air distribution vents to the seatback such that each air distribution vent is situated on opposite sides of the seatback and configured to provide purified air to an inhalation sphere at the passenger seat.

22. The ventilation assembly of claim 20, wherein the seat attachment device comprises one of elastic or a ratchet.

23. The ventilation assembly of claim 18, wherein each fan system is further configured to comprise a female power outlet.

24. The ventilation assembly of claim 18, wherein an air distribution assembly of the number of air distribution assemblies is connected to the plate such that a weight of the air distribution assembly is supported by the plate.

25. The ventilation assembly of claim 18, wherein the fan system comprises at least one of UV sanitizing equipment, an electric filter, or a mechanical air filter.

26. An aircraft that comprises:
a plurality of rows of passenger seats;
a plurality of ventilation assemblies, wherein each ventilation assembly of the plurality of ventilation assemblies is associated with a respective set of passenger seats in the plurality of rows of passenger seats, and wherein each ventilation assembly of the plurality of ventilation assemblies comprises:
    a plate configured to removably connect directly to a seat track in the aircraft and directly to a fan system positioned beneath the respective set of passenger seats and configured to also connect to a power outlet in a passenger seat in the set of passenger seats, wherein the plate comprises a base and a positioning feature that extends orthogonally from the base; and
    a number of air distribution assemblies, each air distribution assembly of the number of air distribution assemblies configured to be removably installed on a seatback of the passenger seat in the set of passenger seats, wherein each air distribution assembly of the number of air distribution assemblies comprises:
    a pair of air distribution vents;
    ductwork configured to receive air from at least one fan system of the number of fan systems and direct air to the pair of air distribution vents; and
    a seat attachment device configured to removably couple the pair of air distribution vents to the seatback such that each air distribution vent is situated on opposite sides of the seatback and configured to provide purified air to an inhalation sphere at the passenger seat.

27. The aircraft of claim 26, wherein each ventilation assembly of the plurality of ventilation assemblies further comprises a manifold configured to distribute air from the fan system to the number of air distribution assemblies.

28. The aircraft of claim 27, wherein the plate comprises:
a base configured to connect to the fan system; and
a positioning feature that extends orthogonally from a base of the plate and is further configured to restrain the manifold.

29. The aircraft of claim 26, wherein each ventilation assembly of the plurality of ventilation assemblies comprises more than one air distribution-assembly.

30. An air distribution assembly configured to be removably installed on a seatback of a passenger seat, wherein the air distribution assembly comprises:
a plate configured to removably connect directly to a track connected to the passenger seat and directly to a of fan system configured to also connect to a power outlet the passenger seat, wherein the plate comprises a base and a positioning feature that extends orthogonally from the base;
a pair of air distribution vents connected to the fan system;
a seat attachment device configured to encircle a portion of the seatback to removably couple the pair of air distribution vents to the seatback such that each air distribution vent is situated on opposite sides of the seatback for providing purified air to a seated passenger; and
ductwork connected to the fan system and configured to receive air from fan system and direct air to the pair of air distribution vents.

31. The air distribution assembly of claim 30, wherein the seat attachment device comprises one of elastic or a ratchet.

32. The air distribution assembly of claim 30, wherein the air distribution assembly is connected to the plate such that a weight of the air distribution assembly is supported by the plate.

33. The air distribution assembly of claim 30, wherein the seat attachment device is adjustable to fit seatbacks of different sizes.

34. The air distribution assembly of claim 30, wherein the air distribution assembly is configured such that when the air distribution assembly is installed on the seatback of the passenger seat, airflows from the pair of air distribution vents converge and blend in front of a nose and mouth of a passenger to form a personal breathing space that envelopes an inhalation sphere, impeding transgression of ambient air from crossing through respective barriers and entering into the personal breathing space, such that the inhalation sphere comprises purified air from the fan system.

35. A ventilation assembly configured to retrofit onto a passenger seat mounted in an aircraft, wherein the ventilation assembly comprises:
a plate configured to removably connect directly to a seat track in the aircraft and directly to a fan system configured to also connect to a power outlet in the passenger seat, wherein the plate comprises a base and a positioning feature that extends orthogonally from the base; and
a number of air distribution assemblies pneumatically connected to the number of fan systems, each air distribution assembly of the number of air distribution assemblies removably installed on a seatback of the passenger seat and configured to provide purified air to an inhalation sphere at the passenger seat.

36. The ventilation assembly of claim 35, wherein each air distribution assembly of the number of air distribution assemblies comprises:
a pair of air distribution vents; and
a seat attachment device configured to encircle a portion of the seatback to removably couple the pair of air distribution vents to the seatback such that each air distribution vent is situated on opposite sides of the seatback.

37. The ventilation assembly of claim 36, wherein each air distribution assembly of the number of air distribution assemblies is configured such that purified airflows from the pair of air distribution vents converge and blend in front of a nose and mouth of a passenger to form a personal breathing space that envelopes an inhalation sphere suffused with a purified air, impeding transgression of ambient air from crossing through respective barriers and entering into the personal breathing space, such that the inhalation sphere comprises purified air supplied to the air distribution assembly by the fan system.

38. The ventilation assembly of claim 35, wherein an air distribution assembly of the number of air distribution assemblies is connected to the plate such that a weight of the air distribution assembly is supported by the plate.

39. A method of providing purified air to an inhalation sphere at a passenger seat in an aircraft, the method comprising:

securing a fan system comprising a purification system directly to a plate directly connected to a seat track beneath the passenger seat and to a power outlet of the passenger seat, wherein the plate comprises a base and a positioning feature that extends orthogonally from the base;

removably connecting ductwork to the fan system and to a seatback of the passenger seat; and running the fan system and drawing air through the purification system and the ductwork and an outlet directing the air toward the inhalation sphere at the passenger seat.

40. The method of claim 39, further comprising a full weight of the fan system bypassing the passenger seat and distributing into the seat-track.

41. The method of claim 40 further comprising:
securing a manifold to the seat track;
connecting the fan system to the manifold such that output from the fan system enters the manifold; and
connecting the ductwork to the manifold.

42. The method of claim 41, further comprising securing the manifold through the positioning feature.

43. The method of claim 39, further comprising extending or contracting an attachment system to encircle a portion of a respective seatback.

44. The method of claim 39, further comprising suffusing the inhalation sphere with purified air via removably connecting a pair of air distribution vents on opposite sides of the seatback.

45. The method of claim 39, further comprising removably connecting air distribution assemblies to a respective passenger seat such that the air distribution assembly is directing purified airflows from a pair of air distribution vents converging and blending in front of a nose and mouth of a passenger, impeding transgression of ambient air from crossing through respective barriers and entering into a personal breathing space and suffusing the inhalation sphere with purified air supplied to the air distribution assembly by fan system.

* * * * *

UNITED STATES PATENT AND TRADEMARK OFFICE
CERTIFICATE OF CORRECTION

| | | |
|---|---|---|
| PATENT NO. | : 12,116,133 B2 | Page 1 of 1 |
| APPLICATION NO. | : 17/658607 | |
| DATED | : October 15, 2024 | |
| INVENTOR(S) | : Ty Aaby Larsen et al. | |

It is certified that error appears in the above-identified patent and that said Letters Patent is hereby corrected as shown below:

In the Claims

Column 27, Claim 11, Line 58, correct "sphere suffused with a purified air comprises purified air." to read --sphere suffused with a purified air.--
Column 29, Claim 30, Line 59, correct "connected to the passenger seat and directly to a of fan" to read --connected to the passenger seat and directly to a fan--

Signed and Sealed this
Twenty-sixth Day of November, 2024

Katherine Kelly Vidal
*Director of the United States Patent and Trademark Office*